United States Patent [19]

Verweij et al.

[11] 4,003,894

[45] Jan. 18, 1977

[54] PREPARATION OF 7-SUBSTITUTED AMINO-DESACETOXYCEPHALOSPORANIC ACID COMPOUNDS

[75] Inventors: Jan Verweij, Leiden; Hong Sheng Tan, Bleiswijk; Hermanus Jacobus Kooreman, Delft, all of Netherlands

[73] Assignee: Gist-Brocades N.V., Delft, Netherlands

[22] Filed: May 5, 1975

[21] Appl. No.: 574,365

Related U.S. Application Data

[63] Continuation of Ser. No. 279,868, Aug. 11, 1972, abandoned.

[30] Foreign Application Priority Data

Aug. 17, 1971 United Kingdom .......... 38637/71
Dec. 21, 1971 United Kingdom .......... 59516/71

[52] U.S. Cl. .................. 260/243 C; 260/239.1; 260/429 R; 260/429.7; 260/448.8 R
[51] Int. Cl.$^2$ ........................... C07D 501/10
[58] Field of Search ............... 260/243 C

[56] References Cited

UNITED STATES PATENTS

| | | | |
|---|---|---|---|
| 3,275,626 | 9/1966 | Morin et al. | 260/243 C |
| 3,536,698 | 10/1970 | Chauvette et al. | 260/243 C |
| 3,573,295 | 3/1971 | Johnson et al. | 260/243 C |
| 3,632,850 | 7/1972 | Garbrecht | 260/243 C |
| 3,637,678 | 1/1973 | Webber et al. | 260/243 C |
| 3,668,202 | 6/1972 | Foster et al. | 260/243 C |
| 3,671,449 | 6/1972 | Jackson | 260/243 C |
| 3,674,775 | 7/1972 | Spry | 260/243 C |
| 3,725,397 | 4/1973 | Graham et al. | 260/243 C |
| 3,725,399 | 4/1973 | Ellerton et al. | 260/243 C |

OTHER PUBLICATIONS

Cotton et al., "Advanced Inorganic Chemistry," 1966, p. 465 (Interscience publishers).

*Primary Examiner*—Nicholas S. Rizzo
*Assistant Examiner*—David E. Wheeler
*Attorney, Agent, or Firm*—Hammond & Littell

[57] ABSTRACT

Process for the preparation of 7-substituted amino-desacetoxycephalosporanic derivatives comprising converting a 6-substituted amino-penicillanic acid sulfoxide into an anhydride of a 6-substituted amino-penicillanic acid sulfoxide, heating the said acid anhydride intermediate at a temperature up to at most 160° C in a dry inert organic solvent with an anhydrous acid which is capable of causing ring expansion of the penam ring to a $\Delta^3$-cephem ring, in the presence of a silicon-containing compound capable of (a) removing water formed during the ring enlargement of the penam structure fast enough to prevent water hydrolysis of the acid anhydride moiety present and (b) forming neutral or basic products on hydrolysis, the aforesaid acid being strong enough not to be, or not to a substantial extent to be, silylated under the reaction conditions employed, and hydrolyzing the resulting compound in situ to form the $\Delta^3$-7-substituted amino-desacetoxycephalosporanic acid as such or as a salt, such as alkali metal, alkaline earth metal or amine salt and to the novel sulfoxide acid anhydrides formed therein.

26 Claims, No Drawings

PREPARATION OF 7-SUBSTITUTED AMINO-DESACETOXYCEPHALOSPORANIC ACID COMPOUNDS

PRIOR APPLICATION

This application is a continuation of copending, commonly assigned application Ser. No. 279,868 filed Aug. 11, 1972, now abandoned.

State of the Art

Penicillins and cephalosporins are compounds which contain respectively the "penam" and "cepham" structures:

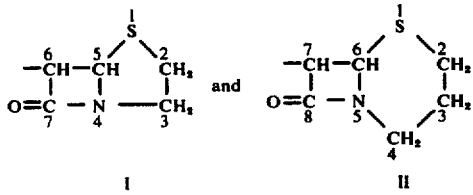

while "cephem" refers to the corresponding ring structure with a double bond, the position of which is indicated by a prefixed "Δ" with superscript denoting the carbon atom of lowest number to which the double bond is connected.

Recently a great amount of interest has been shown in the preparation of $\Delta^3$-cephalosporins, which have antibiotic activity, from penicillins. For example, U.S. Pat. No. 3,275,626 discloses that 7-amino-cepham and -cepham derivatives can be prepared by heating analogous 6-aminopenicillanic sulfoxide derivatives in solution to temperatures of about 80° to 175° C under acid conditions which may be promoted by acetic anhydride or toluene-p-sulfonic acid, for example. This known process which involves heating under acid conditions results in a rearrangement of the heterocyclic ring structure leading to the enlargement of the thiazolidine ring of the penicillanic sulfoxide and the formation, among others, of a thiazine ring which is a structural part of cephalosporin compounds. Several of these cephalosporin compounds possess useful antibiotic activities and are, therefore, very important as therapeutics.

When the ring enlargement process described in the said patent is carried out with a 6-substituted-amino-penicillanic acid sulfoxide, i.e., a compound having the structure I with an acylamido group R—CO— attached to the 6-position wherein R is essentially any organic radical known in penicillin chemistry, oxygen attached to the sulfur atom, two methyl groups attached to the 2-carbon atom, and a carboxy group attached to the 3-carbon atom, or with a salt of such an acid, it is found that the 6-amino-penicillanic acid starting material is decarboxylated during the formation of the cephalosporin and, therefore, the cephalosporin product has no carboxy group attached to the 4-carbon atom of structure II as is required for antibiotically-useful cephalosporin compounds.

However, when esters such as the alkyl, cycloalkyl or phenyl esters of such 6-substituted-amino-penicillanic acid sulfoxides are used as starting materials, the ring enlargement to cephalosporin compounds using the disclosure of the said patent proceeds satisfactorily and the $\Delta^3$-cephem products have an esterified carboxy group attached to the 4-carbon atom. Thus is appears from the said patent that when it is desired to obtain cephalosporins with a free carboxy group attached to the 4-carbon atom, the carboxy group of a 6-substituted-amino-penicillanic acid sulfoxide starting material must first be esterified with a hydrocarbon radical in an initial separate step and the esterifying radical in the cephalosporanic product after the ring enlargement reaction must subsequently be removed by, for example, hydrolysis or by catalytic hydrogenation. This procedure requiring the initial separate formation of a hydrocarbon ester of the 6-amino-penicillanic acid (i.e., an ester with the COO- group joined to a hydrocarbon, e.g., methyl or benzhydryl, or substituted hydrocarbon radical through a carbon atom) necessitates the separation and isolation of at least one intermediate and is disadvantageous in that respect.

OBJECTS OF THE INVENTION

It is an object of the invention to provide a novel process for the preparation of cephalosporanic acids from penicillanic acid sulfoxides which avoids decarboxylation of the penicillanic acid sulfoxide and can obviate the prior art disadvantage of effecting the whole reaction procedure in one stage and in a single vessel, thus being more convenient and easier to operate than the hitherto known process, and which can give rise to good yields directly of $\Delta^3$-cephem compounds which are antibiotically useful.

It is another object of the invention to provide novel anhydrides of 6-substituted amino-penicillanic acid sulfoxides which are useful intermediates.

These and other objects and advantages of the invention will become obvious from the following detailed description.

The Invention

The process of the invention successively involves the formation of anhydride intermediates of 6-substituted amino-penicillanic acid sulfoxides easily hydrolyzable by water alone, and their ring enlargement to $\Delta^3$-desacetoxycephalosporins such as compounds of the structure II with a methyl group attached to the 3-carbon atom, a carboxy group attached to the 4-carbon atom, and a double bond between the 3- and 4-carbon atoms with an acid in the presence of silicon-containing compounds which are capable of reacting rapidly with the water formed during the ring enlargement and give rise to neutral or basic products when hydrolyzed.

The novel process of the invention for the preparation of 7-substituted amino-desacetoxycephalosporanic derivatives comprises converting a 6-substituted amino-penicillanic acid sulfoxide into an anhydride of a 6-substituted amino-penicillanic acid sulfoxide, heating the said acid anhydride intermediate at a temperature up to 160° C in a dry inert organic solvent with an anhydrous acid capable of causing ring expansion of the penam ring to a $\Delta^3$-cephem ring in the presence of a silicon-containing compound capable of (a) removing water formed during the ring enlargement of the penam structure fast enough to prevent water hydrolysis of the acid anhydride moiety present and (b) forming neutral or basic products on hydrolysis, the aforesaid acid being strong enough not to be, at least to a substantial extent, silylated under the reaction conditions employed, and hydrolyzing the resulting compound in situ to form the corresponding $\Delta^3$-7-substituted amino-desacetoxycephalosporanic acid or a salt thereof, e.g., sodium, potassium, calcium or amine salt.

An anhydride of a penicillanic acid or cephalosporanic acid means a penicillanic acid or cephalosporanic acid, the carboxyl group of which is protected so that the protecting group may easily be removed by hydrolysis in a neutral aqueous medium.

The new process may be applied generally to the preparation of 7-substituted amino-desacetoxycephalosporanic acid derivatives of the formula:

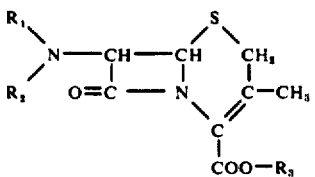

from the corresponding 6-substituted amino-penicillanic sulfoxides of the formula:

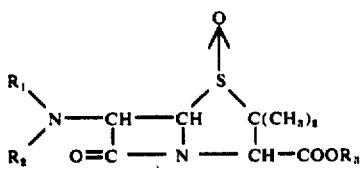

wherein $R_1$ is selected from the group consisting of hydrogen and a group linked to the nitrogen atom by a carbon or sulfur atom, and optionally having substituents not affected by the reaction, $R_2$ is selected from the group consisting of hydrogen, and lower alkyl and phenyl (lower) alkyl and $R_1$ and $R_2$ together with the nitrogen atom to which they are attached collectively represent a heterocyclic group, such as a succinimido, phthalimido, oxazolidinyl or imidazolidinyl which may have one or more substituents not affected by the reaction, and —COOR$_3$ is selected from the group consisting of a. an acid anhydride group wherein $R_3$ is

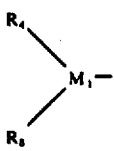

wherein $R_4$ and $R_5$ are the same or different and each is selected from the group consisting of lower alkyl, cycloalkyl radical of 5 to 8 carbon atoms, phenyl, phenylalkyl having 1 to 2 carbon atoms in the alkyl radical, lower alkoxy, lower alkylthio, phenoxy, phenylalkoxy group containing 1 to 2 carbon atoms in the alkoxy radical, halogen and a 6-substituted amino-penicillanylsulfoxide-3-carbonyloxy group and 7-substituted amino-desacetoxycephalosporanyl-4-carbonyloxy group, and $R_4$ and $R_5$ together are the residue of a ring including $M_1$, and $M_1$ is selected from the group consisting of boron, aluminum or phosphorus atoms and b. an acid anhydride group wherein $R_3$ has the formula:

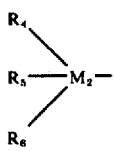

wherein $R_4$, $R_5$ and $R_6$ are the same or different and each is selected from the group consisting of lower alkyl, cycloalkyl of 5 to 8 carbon atoms, phenyl, phenylalkyl having 1 to 2 carbon atoms in the alkyl radical, lower alkoxy, lower alkylthio, phenoxy, phenylalkoxy group having 1 to 2 carbon atoms in the alkoxy radical, halogen and a 6-substituted amino-penicillanyl sulfoxide-3-carbonyloxy group and 7-substituted amino-desacetoxycephalosporanyl-4-carbonyloxy group and $R_4$ and $R_5$ together are the residue of a ring including $M_2$ and $R_4$ with $R_5$ or $R_6$ together are selected from the group consisting of =O and =S, and $M_2$ is selected from the group consisting of silicon, sulfur, germanium and tin atoms, or a carbon atom when $R_4$ and $R_6$ together are selected from the group consisting of =O and =S.

c. an acid anhydride group wherein $R_3$ has the formula:

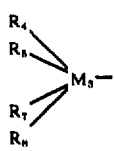

wherein $R_4$ and $R_5$ are the same or different and have the above definition, and $R_7$ and $R_8$ are the same or different and are selected from the group consisting of halogen, a 6-substituted amino-penicillanyl sulfoxide-3-carbonyloxy and 7-substituted amino-desacetoxycephalosporanyl-4-carbonyloxy and $R_7$ and $R_8$ together are the residue of a ring including $M_3$, or together are selected from the group consisting of =S and =O, and $M_3$ is selected from the group consisting of phosphorous and tungsten atoms, d. an acid anhydride group, wherein $R_3$ has the formula:

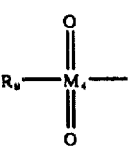

wherein $R_9$ is selected from the group consisting of lower alkyl, cycloalkyl of 5 to 8 carbon atoms, phenyl, phenylalkyl having 1 to 2 carbon atoms in the alkyl radical, lower alkoxy, lower alkylthio, phenoxy, or phenylalkoxy group having 1 to 2 carbon atoms in the alkoxy radical, and $M_4$ is a sulfur atom and e. a group wherein $R_3$ is selected from the group consisting of hydrogen and a cation which is preferably an alkali metal or alkaline earth metal such as sodium, potassium or calcium, or derived from an amine such as triethylamine or cyclohexylamine.

The term "lower" as applied herein to alkyl, alkoxy and alkylthio group means that the group has 1 to 6 carbon atoms, and the phenyl groups or moieties within the definitions of $R_4$, $R_5$, $R_6$ and $R_9$ may optionally carry one or more substituents selected from the group consisting of halogen, lower alkyl, lower alkoxy and di(lower)alkylamino.

Preferably the group —$COOR_3$ in the compounds of formulae III and IV is an acid anhydride group in which $R_3$ has formula V wherein $R_4$ and $R_5$ are as hereinbefore defined and $M_1$ is a phosphorus, aluminum or boron atom, or $R_3$ has formula VI wherein $R_4$, $R_5$ and $R_6$ are as hereinbefore defined and $M_2$ is a silicon, germanium or tin atom, or $R_4$ and $R_5$ or $R_6$ together are =O and $M_2$ is a carbon atom, and preferably, $R_5$ is an alkyl group. When $M_2$ is a silicon atom, $R_3$ is preferably a silyl radical of the formula $(X_1 \ X_2 \ X_3)$ — Si—, wherein $X_1$, $X_2$ and $X_3$ are the same or different and are selected from the group consisting of halogen, lower alkyl, lower alkoxy, phenyl, phenylalkyl having 1 to 2 carbon atoms in the alkyl radical, cycloalkyl of 5 to 8 carbon atoms and a 6-substituted aminopenicillanyl sulfoxide-3-carbonyloxy and 7-substituted amino-desacetoxycephalosporanyl-4-carbonyloxy group, the group $X_1$, $X_2$ and $X_3$ when not halogen or alkyl being optionally substituted with at least one member of the group consisting of halogen, lower alkyl, lower alkoxy and di(lower) alkylamino. Especially preferred as a silyl radical is a tri(lower alkyl)silyl group and more particularly trimethylsilyl.

Reagents for the protection of the carboxylic function of starting materials of formula IV are those of formulae V, VI, VII and VIII and of which the free bonds linked to the atoms represented by the M symbols have been saturated by an anhydride group, preferably a halogen atom. These reagents when reacting with the 6-substituted amino-penicillanic acid sulfoxide give rise to the substitution of the hydrogen atom, which atom will combine with the activating group (e.g. a halogen atom) of the reagent thus forming an acid. This acid then serves as the acid means for the ring enlargement reaction.

Examples of compounds containing the group of formula V are substances that can be considered as acid derivatives such as $BCl_3$, $BBr_3$, $AlCl_3$, $AlBr_3$, $PCl_3$, $PBr_3$, $C_4H_9BCl_2$, $(C_4H_9)_2BCl$, $(C_2H_5)_2AlCl$, $(C_4H_9)_2AlCl$, $C_6H_5PCl_2$,

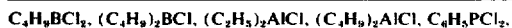
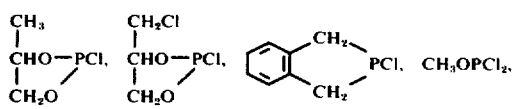
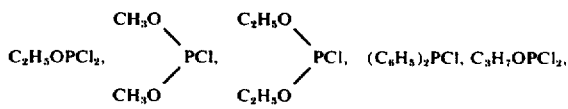
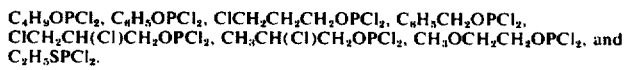

Examples of compounds containing the group of formula VI that also can be considered as acid derivatives are substances such as $COCl_2$, $CSCl_2$, $C_2H_5OCOBr$,

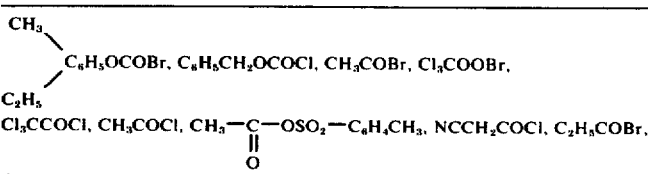
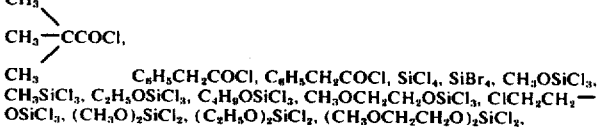
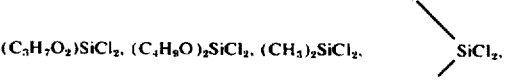
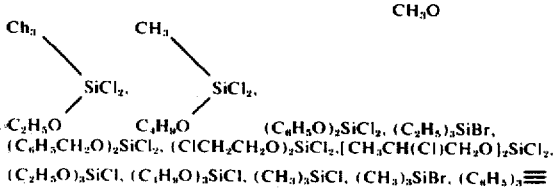

-continued

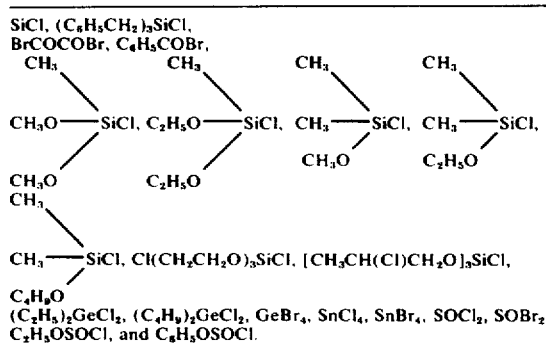

SiCl, (C₆H₅CH₂)₃SiCl, BrCOCOBr, C₆H₅COBr,

Ch(CH₂CH₂O)₃SiCl, [CH₃CH(Cl)CH₂O]₃SiCl, (C₂H₅)₂GeCl₂, (C₄H₉)₂GeCl₂, GeBr₄, SnCl₄, SnBr₄, SOCl₂, SOBr₂ C₂H₅OSOCl, and C₆H₅OSOCl.

Other silicon containing reagents usable for the protection of the carboxylic function of the starting material belong to the list of substances necessarily present for removing the water formed during the ring enlargement which substances are enumerated further on in the specification.

Examples of the reagents containing the group of formula VII are phosphorus acid derivatives such as $PCl_5$,

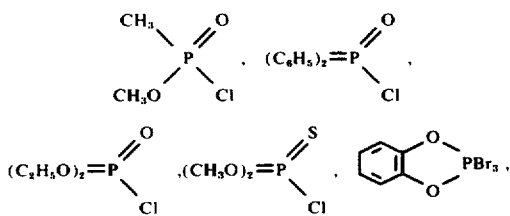

$C_6H_5POCl_2$, $CH_3OPOCl_2$, $C_2H_5OPOCl_2$, $C_3H_7OPOCl_2$, $C_4H_9OPOCl_2$, $ClCH_2CH_2OPOCl_2$, $CH_3OCH_2CH_2OPOCl_2$, $C_6H_5OPOCl_2$, $C_2H_5SPOCl_2$, and tungsten containing compounds such as $WBr_5$.

Compounds containing the group formula VIII are acid derivatives such as $C_2H_5OSO_2Cl$, $C_4H_9OSO_2Cl$, $C_6H_5SO_2Cl$, $CH_3C_6H_4SO_2Cl$, $C_6H_5OSO_2Cl$ and $C_6H_5CH_2OSOCl$.

Of the preferred protecting reagents, it is advantageous to employ substances which are widely known and used in chemistry such as phosphorus trihalides, phosphorus pentahalides, tri(lower alkyl) halosilanes, di(lower alkyl)dihalosilanes, and carboxylic acid halides. The most preferred reagents are phosphorus containing compounds such as phosphorus tribromide and phosphorus pentabromide and silicon containing compounds such as tri(lower alkyl)bromosilanes, e.g. trimethylbromosilane, di(lower alkyl)dibromosilanes, e.g. dimethyl dibromosilane, N,O-bis(trialkylsilyl)acetamides, e.g. N,O-bis(trimethylsilyl)acetamide.

The preferred molecular proportions of the carboxylic protecting reagents in relation to each mole of 6-substituted amino-penicillanic acid sulfoxide employed are 0.25 to 2 equivalents of reagent and preferably ⅓ to 1 equivalent. By the term "one equivalent" is meant the number of moles of reagent theoretically required to protect the carboxy group of one mole of benzylpenicillanic acid sulfoxide.

The group represented by $R_1$ in formulae III and IV may be any group hitherto disclosed in relation to cephalosporins and penicillins or analogues thereof. For example, $R_1$ can be an alkanoyl group of up to 20 carbon atoms, phenyl (lower)alkanoyl, phenoxy(lower)alkanoyl, phenyl(lower)alkyloxycarbonyl, (lower)alkanoylaminocarbonyl, (lower)alkoxy (lower)alkanoyl, salicyl optionally substituted by one or two halogen atoms, phenoxyphenyl(lower)alkanoyl, isoxazolylcarbonyl, benzoyl, naphthoyl, formyl, oxazolidinyl, phenyl-α-amino(lower)alkanoyl, thienyl-or furyl-(lower)alkanoyl, thienyl-or furyl-α-amino-(lower)alkanoyl, phenylthio(lower)alkanoyl, 2-benzofuranyl-(lower)alkanoyl, benzenesulfonyl, or 1-piperidinosulfonyl. The phenyl and heterocyclyl radicals of such groups may carry substituents such as halogen, lower alkyl, protected carboxy, phenyl(lower)alkoxy, protected amino, nitro, cyano, trifluoromethyl and methylthio. For example, the symbol $R_2$ may be hydrogen, methyl, ethyl, isobutyl, or benzyl. Moreover, the symbols $R_1$ and $R_2$ together with the nitrogen atom to which they are attached may form a heterocyclic group such as phthalimido.

Suitable groups represented by the grouping

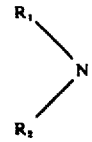

in formulae III and IV are benzyloxycarbamoyl, phenylacetamido, phenoxyacetamido, 3-acetyl-ureido, (3,5-dichlorosalicyl)amino, 2-phenoxypropionamido, 2-phenoxybutyramido, 2-phenoxyphenylacetamido, 5-methyl-3-phenyl-4-isoxazolicarboxamido, 5-methyl-3-(o-chlorophenyl)-4-isoxazolecarboxamido, 5-methyl-3-(2,6-dichlorophenyl)-4-isoxazolecarboxamide, 2,6-dimethoxybenzamido, 2-ethoxy-1-naphthamido, 2-(o-aminobenzamido)phenylacetamido-N-methyl, 2-(2-amino-5-nitrobenzamido)phenylacetamido-N-methyl N-benzylformamido, N-methyl-2-phenoxyacetamido, N-methyl-2-phenylacetamido, N-ethyl-2-phenylacetamido, N-isobutyl-2-phenoxyacetamido, 2-benzylidene-4,5-dioxo-3-oxazolidinyl, 2-butylsuccinimido, 2,2-dimethyl-5-oxo-4-phenyl-1-imidazolidinyl phthalimido, α-amino-α-(1-cyclohexa-1,4-dienyl)acetamido, α-aminophenylacetamido, α-amino-2-thienylacetamido, 2-thienzlacetamido, 3-thienylacetamido, 2-furylacetamido, 4-chlorophenylacetamido, 3-bromophenylacetamido, 3-nitrophenylacetamido, 4-nitrophenylacetamido, 3-trifluoromethyl-phenylacetamido, 4-cyanophenylacetamido, 4-methylthiophenylacetamido, 3- chlorophenylthioacetamido, 2-benzofuranylacetamido, benzenesulfonamido, benzenesulfonylaminoacetamido, p-bromobenzenesulfonamido, and 1-piperidinosulfonamido. Preferred groupings represented by $R_1R_2N-$ are phenylacetamido and phenoxyacetamido.

When it is desired to obtain a desacetoxycephalosporanic derivative of formula III in which $R_1R_2N-$ is e.g. α-aminophenylacetamido, the free amino group of the corresponding 6-substituted-amino-pencillanic sulfoxide starting material of formula IV should be protected during the ring enlargement by, for example, a benzyloxycarbonyl group which can readily be subsequently removed to leave the free amino group. A free carboxylic acid group in the 6-acyl side chain can be protected for instance by esterification or preferably by acid anhydride formation, thereby consuming an additional amount of the reagent responsible for the acid anhydride formation of the carboxylic group connected to the thiazolidino ring.

The silicon containing compound necessarily present in the reaction mixture to remove the water formed during the ring enlargement of the penam structure is preferably a compound of a formula selected from the group consisting of

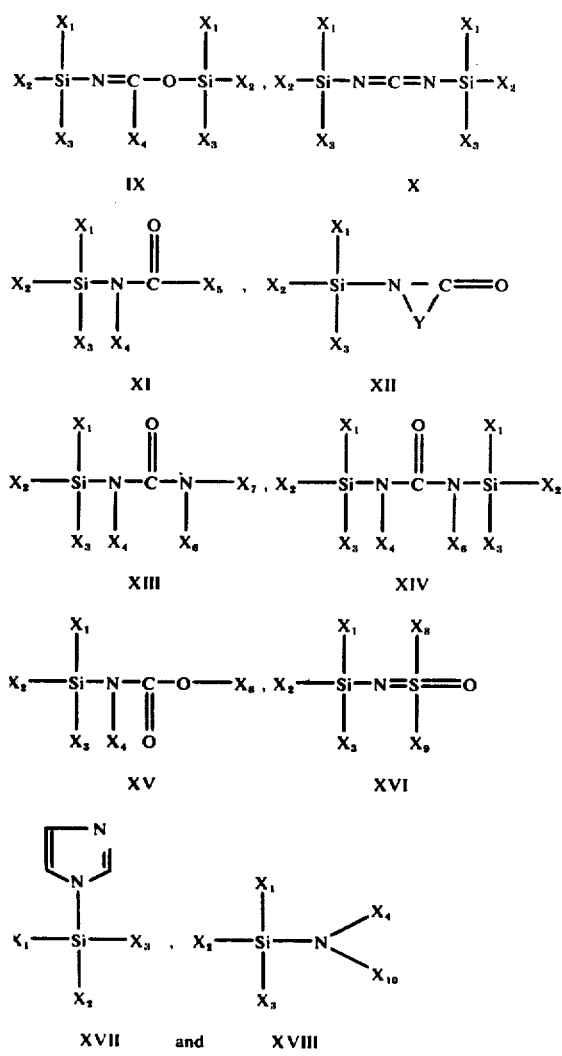

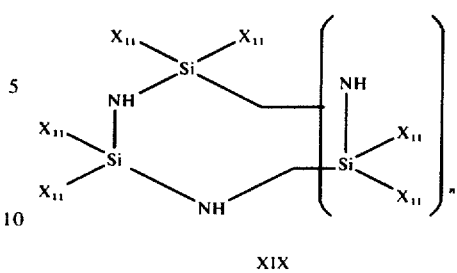

XIX wherein $X_1$, $X_2$ and $X_3$ are as defined above excluding the possibility that any of the symbols is a 6-substituted amino-pencillanyl sulfoxide-3-carbonyloxy or 7-substituted amino-desacetoxycephalosporanyl-4-carbonyloxy group; $X_4$, $X_5$, $X_6$ and $X_7$ are individually selected from the group consisting of hydrogen and hydrocarbon group of 1 to 8 carbon atoms, with no aliphatic unsaturation and $X_6$ and $X_7$ together with the nitrogen atom to which they are attached may form a 5- or 6- membered heterocyclic group which may contain a second hetero atom selected from oxygen and nitrogen, with the provisos that $X_6$ and $X_7$ together contain not more than 18 carbon atoms, and, $X_6$ is alkyl with a tertiary carbon atom linked to the depicted nitrogen atom, $X_7$ is hydrogen, or $X_4$ and $X_6$ together with the nitrogen atoms to which they are attached and the carbonyl group complete a 5- or 6- membered heterocyclic group with an ethylene or tri-methylene group in the ring; $X_8$ and $X_9$ each are hydrocarbon of 1 to 8 carbon atoms, with no aliphatic unsaturation (preferably alkyl), $X_{10}$ is selected from the group consisting of hydrogen, hydrocarbon of 1 to 8 carbon atoms with no aliphatic unsaturated and $-Si$ ($X_1$ $X_2$ $X_3$); $X_{11}$ is alkyl of 1 to 8 carbon atoms; Y is alkylene of 3 to 18 carbon atoms with at least 3 and not more than 5 carbon atoms between the nitrogen atom and the carbonyl group to which Y is attached; and n is 1 or 2.

Examples of silicon-containing compounds of formulae IX to XVII are N,O-bis(trimethylsilyl)acetamide, N,O-bis(trimethylsilyl)trifluoroacetamide, N,N-bis(-trimethylsilyl)carbodiimide, N-(trimethylsilyl)-acetamide, N-methyl-N-(trimethylsilyl)acetamide, N-methyl-N-(trimethylsilyl)formamide, N-(trimethylsilyl)-2-pyrrolidone, N-(triethylsilyl)urea, N,N'-bis(trimethylsilyl)urea, N-(triphenylsilyl)-ethylcarbamate, trimethylsilyldimethylsulfoximide, N-trimethylsilyl-N-methyltrifluoroacetamide and trimethylsilylimidazole. These silicon-containing compounds produce on reaction with water neutral compounds which do not affect the course of the reaction or interfere with separation of the Δ³-desacetoxycephalosporanic product.

Examples of silicon-containing compounds of formulae XVIII and XIX are triphenylsilylamine, N-ethyltriethylsilylamine, N-(trimethylsilyl)diethylamine, hexamethyldisilazane, hexamethylcyclotrisilazane and octamethyl cyclotetrasilazane. These silicon-containing compounds produce, on reaction with water, basic compounds.

The silicon-containing compounds preferably employed in the process of the invention are those of formulae IX to XVII. The most preferred silicon-containing compounds used in the process are N,O-bis(-trimethylsilyl)acetamide and N,N'-bis(trimethylsilyl)urea (i.e. the compounds of formulae IX and XIV in which all the X symbols represent methyl groups)

which can react very rapidly with any water formed during ring-expansion to yield neutral products such as hexamethyldisiloxane and acetamide or urea, and thus avoid decomposition of the acid anhydride function by the formed water during ring expansion.

The amount of silicon-containing compound added to the reaction mixture must be sufficient to remove completely the water formed during the process and also, if necessary, to silylate beforehand any free carboxy group in the initial penicillin compound. Thus, when starting with a 6-substituted-aminopenicillanic acid sulfoxide and using a silicon compound of formula IX, at least one and a half molecular equivalents of silicon compound per mole of penicillanic acid sulfoxide are required, one half mole to act as silyl donor for the carboxy group and the rest to eliminate the water formed. However, when starting with an acid anhydride of the 6-substituted aminopenicillanic sulfoxide only at least one mole of the silicon compound will be needed to remove the water. Preferably, at least 2 to 4 molecular equivalents of the silicon compound are used for each mole of penicillin sulfoxide.

Acids which may be used in the process of the invention to effect ring expansion of the penam ring are those which are not silylated, or not to a substantial extent silylated, by the silicon-containing compound added to the reaction mixture under the reaction conditions employed. Suitable acids are hydrogen bromide, hydrogen chloride, toluene-p-sulfonic and concentrated sulfuric acid. Other suitable acids are hydrogen iodide, perchloric acid, periodic acid, nitric acid, chloric acid, iodic acid, selenic acid, substituted acetic acids such as bromoacetic acid, trichloroacetic acid, and trifluoroacetic acid, substituted sulfonic acids such as trichloromethylsulfonic acid and trifluoromethylsulfonic acid, naphthalenesulfonic acid, oxalic acid, picric acid, and C—H acids such as tris-(ethylsulfonyl)methane, pentacyanopropane, tetracyanopropene, pentacyanocyclopentadiene, tetracyanocyclopentadiene and tricyanocyclopentadiene and dinitroacetonitrile, and in general compounds containing cyano, nitro and-/or methoxy-carbonyl groups. A preferred strong acid is hydrogen bromide.

The acid can be incorporated as such into the reaction mixture but advantageously, the acid is combined with a nitrogen containing base forming an acid addition salt complex. Suitable bases are aliphatic, cycloaliphatic, aromatic or heterocyclic amines, such as hexamethylenetetramine, aniline, diphenylamine, N-methylaniline, dimethylaniline, pyridine and quinoline, and pyridine or quinoline substituted by, for example, at least one member of the group consisting of lower alkyl, aralkyl, aryl or mono-or di(lower)alkylamino group such as picolines, 2-ethylpyridine, 2-propylpyridine, 2,3-dimethylpyridine, 2,5-dimethylpyridine, 2,6-dimethylpyridine, collidines and 2-dimethylaminopyridine, quinoline, isoquinoline, 3-methylisoquinoline, pyrazole, imidazole, or N-methylimidazole. Preferred bases are pyridine, substituted pyridines, quinoline, substituted quinolines, imidazole and substituted imidazoles. An excess of the base in relation to the amount of acid is preferably employed.

The acid-nitrogen organic base complex may be formed in situ in the reaction mixture by initially protecting a 6-substituted aminopenicillanic acid sulfoxide starting material in solution in the dry inert organic solvent by reaction with an acid radical containing compound, such as halogen containing compound e.g. phosphorus trichloride, phosphorus pentachloride, acetyl bromide, propionyl bromide, trimethylchlorosilane, dimethyldichlorosilane, trimethylbromosilane or triethylbromosilane. The hydrogen halide so formed in this initial stage is preferably bound by a base because the course of the acid anhydride formation will proceed more smoothly and the pencillanic sulfoxide ring structure is very sensitive to the free strong acid.

In principle, all bases with the exception of bases containing a hydroxy group are suitable to bind this acid such as potassium carbonate or the amine component of the penicillanic acid sulfoxide cyclohexylamine salt, but preferably, nitrogen-containing bases soluble in the organic solvent employed and having a pKa between 4 and 10 are employed. The hydrogen halide formed initially can supplement or actually be the acid necessary to effect ring enlargement of the penicillin sulfoxide.

The presently preferred molecular proportions of the substances included in the reaction mixture in relation to each mole of 6-substituted-aminopenicillanic acid sulfoxide employed are ¼ to 4 moles of acid, preferably about ⅓ to 1 mole; ¼ to 4 equivalents of carboxylic protecting reagent preferably ⅓ to 1 equivalent; at least 2 equivalents of silicon-containing compound preferably 3 to 7 equivalents; or, when an acid nitrogen-containing complex is used, 0.1 to 10 moles of acid-base complex, preferably 0.25 to about 4 moles; 0.25 to 2 equivalents of carboxylic protecting reagent preferably ⅓ to 1 equivalent; at least 2 equivalents of silicon-containing compound preferably 3 to 7 equivalents; and preferably, an additional quantity of the base itself of, for example, from 1 to 10 moles, the quantity of additional base preferably increasing in direct relationship with the amount of acid-base complex employed. By the term "one equivalent" is meant the number of moles of carboxylic protecting reagent or silyl compound theoretically required to react with one mole of benzylpenicillanic acid sulfoxide.

The acid anhydride formation and the ring enlargement reaction are carried out in a dry inert organic solvent. Suitable solvents ar acetonitrile, chlorobenzene, toluene, diethylmethylsulfonamide, dimethylformamide, N,N-dimethylacetamide, 1,2-dimethoxyethane, dioxane, triethyleneglycol diethyl ether, tetraethyleneglycol diethyl ether, nitrobenzene, benzylcyanide, butyl acetate, isoamylacetate, diethyloxalate, anisole, benzene, carbon tetrachloride, dimethylsulfoxide, methyl ethyl ketone, methyl or ethyl isobutyl ketone, and haloalkanes such as 1,2-dichloroethane, 1,1-dichloroethane, 1-bromo-1-chloroethane, 1,2,3-trichloropropane, methylene chloride and chloroform. A preferred solvent is dioxane.

The ring enlargement process is effected at a temperature between 50° and 160° C. and is advantageously carried out at a temperature between 60° and 130° C, and most preferably within the range 70° to 110° C. The reaction temperature should be kept below 160° C. in order to minimize the formation of decomposition products. Generally, the reaction temperature and reaction times are interrelated to obtain good yields of the desacetoxycephalosporanic derivatives. Lower temperatures require longer reaction times and higher temperatures require shorter reaction times, e.g. at 80°, 90° and 100° C., the reaction times may be about 24 hours, 10 hours and 6 hours, respectively.

In a preferred aspect of the invention, for each mole of penicillanic acid sulfoxide such as benzylpenicillin sulfoxide, there is employed 1 to 4 moles of acid, preferably hydrogen bromide or hydrogen chloride, 1.5 to 15 moles of nitrogen-containing base, preferably α-picoline the amount of base always exceeding that of acid, and 2 to 4 moles of N,O-bis(trimethylsilyl)acetamide, and the reaction is carried out at a temperature of 80° to 110° C in a dry inert organic solvent, preferably dioxane.

In another preferred aspect of the invention, for each mole of pencillanic acid sulfoxide, there are employed ⅓ to 1 equivalent of acetyl bromide or phosphorus tribromide, 1.5 to 15 moles of nitrogen-containing base, preferably α-picoline the amount of base always exceeding that of the developing acid, and 1.5 to 3 moles of N,O-bis-(trimethylsilyl)acetamide or N,N'-bis(trimethylsilyl)urea.

On termination of the ring enlargement reaction, the $\Delta^3$-desacetoxycephalosporanic product is hydrolyzed in the reaction mixture and the resulting $\Delta^3$-desacetoxycephalosporanic acid as such or as its salt is recovered by any convenient method such as extraction and/or crystallization. Thus, when the reaction is carried out in an organic solvent immiscible with water, the reaction mixture after cooling may be extracted with water at a pH of 7 adjusted thereto with a dilute aqueous potassium hydroxide solution for example. From the aqueous solution, after washing with an organic medium such as butyl acetate, the $\Delta^3$-desacetoxycephalosporanic acid (e.g. the 7-phenylacetamido derivative) or salt thereof may be obtained as follows:

a. by addition of an aqueous solution of an acid and collection of the precipitated desacetoxycephalosporanic acid;

b. by extraction with an organic solvent at a pH below 4.5 and concentration of the extract to crystallization of the acid;

c. by addition of n-butanol, removal of the water and crystallization of the potassium salt of the acid from the butanolic solution;

d. by extraction with an organic solvent at a pH below 4.5, then addition of an alkali metal salt such as potassium acetate or a solution of an alkali metal salt such as potassium 2-ethylhexanoate or amine such as triethylamine or cyclohexylamine in an organic solvent, and collection of the precipitated alkali metal or amine salt of the acid, or e. by extraction with an organic solvent at a pH below 4.5 and precipitation of the desacetoxycephalosporanic acid by addition of an apolar organic medium such as diethyl ether or cyclohexane.

When the reaction is carried out in an organic solvent miscible with water, the $\Delta^3$-desacetoxycephalosporanic derivative may be separated by pouring the reaction mixture into water and addition of an organic solvent. Sufficient water and organic solvent are required to give separation of the mixture into two layers. The organic layer is re-extracted with water at pH 7 and the combined aqueous layers are washed with an organic medium such as butyl acetate and subsequently treated as indicated hereinbefore under procedures (a) to (e) to separate the $\Delta^3$-desacetoxycephalosporanic acid or salt thereof. Alternatively, on termination of the reaction, the organic solvent may be evaporated in vacuo, the amorphous residue dissolved in a water-immiscible solvent and water added. After adjustment of the pH to 7, the organic phase is discarded. The aqueous solution is washed with an organic medium and subsequently treated as indicated hereinbefore under procedures (a) to (e). The reaction mixture may also be poured into an aqueous acid solution at a pH of about 2 with stirring and the precipitated desacetoxycephalosporanic acid collected by filtration.

The yields of $\Delta^3$-desacetoxycephalosporanic acids obtained by the process of the invention will vary depending upon the reagents and reaction conditions employed but conversion yields in excess of 45% based on the amount of penicillin sulfoxide employed are generally obtained and the conversion yields can be as high as 70% and even over 90%.

The 6-substituted-aminopenicillanic acid sulfoxides employed as starting materials in the process of the invention can be obtained by treatment of the corresponding 6-substituted-aminopenicillanic acids with an oxidizing agent by known methods. For this purpose, the 6-substituted amino-penicillanic derivative is treated in an inert organic solvent or water with a substance affording active oxygen such as sodium periodate, a per-acid, hydrogen peroxide or iodosobenzene in a quantity sufficient to oxidize the thiazolidine sulfur atom to an —SO—group. The resulting sulfoxide can be readily recovered from the reaction mixture by methods known per se. The acid anhydrides of the 6-substituted amino-penicillanic acid sulfoxides can be obtained from the acids or salts by methods known per se, and are preferably in situ prepared in the reaction medium used for the ring enlargement, for instance with the silicon-containing compound employed as the dehydration agent for removing water formed during the ring enlargement of the penam structure.

The novel 6-substituted aminopenicillanic acid anhydrides have the formula:

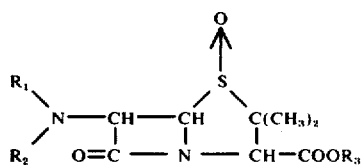

IV wherein (a) $R_3$ has the formula:

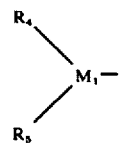

V wherein $R_4$ and $R_5$ are the same or different and are selected from the group consisting of lower alkyl, cycloalkyl of 5 to 8 carbon atoms, phenyl, phenylalkyl having 1 to 2 carbon atoms in the alkyl radical, lower alkoxy, lower alkylthio, phenoxy, phenylalkoxy having 1 to 2 carbon atoms in the alkoxy radical, halogen and a 6-substituted aminopenicillanyl sulfoxide-3-carbonyloxy group and 7-substituted-aminodesacetoxycephalosporanyl-4-carbonyloxy, and $R_4$ and $R_5$ together represent the residue of a ring including the atom $M_1$, and $M_1$ is a boron, aluminum or phosphorus atom;

b. $R_3$ has the formula:

-continued

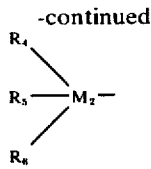

VI wherein $R_4$, $R_5$ and $R_6$ are the same or different and are selected from the group consisting of lower alkyl, cycloalkyl of 5 to 8 carbon atoms, phenyl, phenylalkyl having 1 to 2 carbon atoms in the alkyl radical, lower alkoxy, lower alkylthio, phenoxy or phenylalkoxy having 1 to 2 carbon atoms in the alkoxy radical, halogen and a 6-substituted-aminopenicillanyl sulfoxide-3-carbonyloxy group and 7-substituted-amino-desacetoxycephalosporanyl-4-carbonyloxy group, or $R_4$ and $R_5$ together represent the residue of a ring including $M_2$, or $R_4$ or $R_5$ and $R_6$ together are selected from the group consisting of $=O$ and $=S$ and $M_2$ is a sulfur, germanium, or tin atom, or a carbon atom when $R_4$ and $R_6$ together are $=O$ or $=S$, c. $R_3$ has the formula:

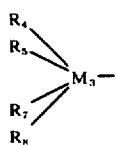

VII wherein $R_4$ and $R_5$ are the same or different and have the above definition and $R_7$ and $R_8$ are the same or different and are selected from the group consisting of halogen, 6-substituted amino-penicillanyl sulfoxide-3-carbonyloxy and 7-substituted amino-desacetoxycephalosporanyl-4-carbonyloxy group, and $R_7$ and $R_8$ together are the residue of a ring including $M_3$, and together are selected from the group consisting of $=O$ and $=S$ and $M_3$ is a phosphorus or tungsten atom, d. $R_3$ has the formula:

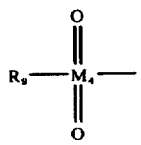

VIII wherein $R_9$ is selected from the group consisting of lower alkyl, cycloalkyl of 5 to 8 carbon atoms, phenyl, phenylalkyl having 1 to 2 carbon atoms in the alkyl radical, lower alkoxy, lower alkylthio, phenoxy, phenylalkoxy having 1 to 2 carbon atoms in the alkoxy radical, and $M_4$ is a sulfur atom.

In a preferred aspect of the invention, the 6-substituted-aminopenicillanic acid sulfoxide employed as starting material is obtained from a penicillin which can be easily prepared by fermentation such as benzylpenicillin or phenoxymethylpenicillin, but other semi-synthetically prepared penicillins are also suitable. After the ring enlargement to the corresponding $\Delta^3$-desacetoxycephalosporanic derivative, the 7-N-acyl group may, if desired, be replaced by another one by methods known per se by deacylation and subsequent reacylation of the 7-amino group.

The term "methods known per se" means methods heretofore used or described in the literature. It is to be noted that the term "lower" as applied herein to alkyl, alkoxy, and alkanoyl groups indicates that the group in question contains at most 6, and preferably not more than 1 or 2 carbon atoms. In the following Examples where the yield of $\Delta^3$-7-phenylacetamido-desacetoxycephalosporanic acid was estimated by microbiological assay, the acid is obtained by treating the reaction mixture in a manner similar to Example I.

In the following examples there are described several preferred embodiments to illustrate the invention. However, it should be understood that the invention is not intended to be limited to the specific embodiments.

EXAMPLE I 195 ml of dioxane, 25 ml (102 mmol) of N,O-bis-(trimethylsilyl) acetamide, 6 ml (61 mmol) of α-picoline and 5.2 ml of a 5.8 molar solution of (30 mmol of α-picoline hydrobromide) of α-picoline hydrobromide in dichloromethane were added successively to 10.5 g (30 mmol) of benzylpenicillin sulfoxide to form in situ the trimethylsilyl derivative of benzylpenicillin sulfoxide and the mixture was then refluxed for 6 hours at 102° C.

The reaction mixture was cooled to 20° C and then poured into 1500 ml of ice-water. Then, 650 ml of ethyl acetate and 50 ml of butyl acetate were added thereto and, with stirring, the pH was adjusted to 7 with 4N potassium hydroxide solution. The mixture was allowed to separate and the organic layer was set aside. The aqueous layer was washed with 300 ml of ethyl acetate and 50 ml of butyl acetate. The resulting organic layer was combined with the one obtained before and the combination was re-extracted with 200 ml of a 0.75 molar potassium phosphate aqueous solution buffered to pH 7. The extract was added to the main aqueous solution and this combined aqueous mixture contained 9.2 g (83% yield) of the potassium salt of $\Delta^3$-7-phenylacetamido-desacetoxycephalosporanic acid, i.e. $\Delta^3$-benzyl-desacetoxycephalosporin as determined by microbiological assay using Escherichia coli as the test microorganism.

After adding 500 ml of butyl acetate to the aqueous solution, the mixture was stirred and the pH was adjusted to 2 with 4N sulfuric acid. The mixture was allowed to stand and the organic extract was separated. The aqueous layer was re-extracted with 250 ml of butyl acetate and the combined butyl acetate extracts were filtered with a water-repellant filter. The aqueous layer, which still contained some $\Delta^3$-7-phenylacetamido-desacetoxycephalosporanic acid, was discarded and to the butyl acetate solution 2.65 g (27 moles) of anhydrous, finely powdered potassium acetate were then added with rapid stirring. After stirring for 3 hours at room temperature, the precipitate was isolated by filtration, washed with a little butyl acetate and dried in vacuo at 30° C to obtain 10.2 g of the potassium salt of $\Delta^3$-7-phenylacetamido-desacetoxycephalosporanic acid, with a purity of 85% as estimated by microbiological assay (yield 23.5 mmoles, 78% yield).

$\lambda$ max ($H_2O$): 262 nm. ($E_1^{1\%}$ $_{cm}$: 175).

The structure was confirmed by IR and PMR spectra.

The analysis of the PMR spectrum was as follows:

PMR (as the potassium salt in D₂O, values in ppm) δ : 1.94 (s, 3); 2.99 (d. J= 18 Hz,1); 3.44 (d, J=18 Hz,1); 3.62 (s, 2); 4.97 (d, J=4.5 Hz,1); 5.58 (d, J=4.5 Hz, 1); 7.27 (s,5).

The sodium salt of 2,2-dimethyl-2-silapentyl-5-sulfonate was used as internal reference.

EXAMPLE II a. 1.05 g (3 mmoles) of benzylpenicillin sulfoxide were added to a mixture of 20 ml of a solution of 3.0 mmoles of hydrogen bromide in dioxane and 2.5 ml (10 mmol) of N,O-bis(trimethylsilyl)acetamide to form the trimethylsilyl derivative of benzylpenicillin sulfoxide in situ. The reaction mixture was heated at 102° C and the reaction was followed by thin layer chromatography. After 6 hours, there was no penicillin sulfoxide left in the reaction mixture. Samples of 5 ml were taken and poured into 35 ml of a 0.75 molar potassium phosphate aqueous solution buffered to pH 7. The aqueous solution was washed with 10 ml of ethyl acetate and diluted with water to 50 ml. The amount of the potassium salt of Δ³-7-phenylacetamido-desacetoxycephalosporanic acid in the aqueous solution was estimated by a direct microbiological assay, using *Escherichia coli* as the test microorganism. After 6 hours, the yield of Δ³-7-phenylacetamido-desacetoxycephalosporanic acid was 47%.

b. The experiment described under (a) was repeated except that 18 ml of toluene and 2 ml of a 1.5 molar solution of hydrogen bromide in dioxane were used instead of 20 ml of dioxane to obtain a 46% yield of Δ³-7-phenylacetamido-desacetoxycephalosporanic acid as estimated by microbiological assay.

c. The experiment described under (a) was repeated except that an additional amount of 0.9 ml (9 mmoles) of α-picoline was used to obtain a 82% yield of Δ³-7-phenylacetamido-desacetoxycephalosporanic acid as estimated by microbiological assay.

EXAMPLE III 20 ml of dioxane, 3.2 ml (13 mmol) of N,O-bis-(trimethylsilyl)acetamide, and 0.57 g (3 mmoles) of p-toluene sulfonic acid were successively added to 1.05 g (3 mmol) of benzylpenicillin sulfoxide to form in situ the trimethylsilyl derivative of benzylpenicillin sulfoxide and the mixture was then refluxed for 6 hours at 101° C after which no sulfoxide remained. The reaction mixture was worked up as in Example II to obtain a 41% yield of Δ³-7-phenylacetamido-desacetoxycephalosporanic acid as estimated by microbiological assay.

EXAMPLE IV a. A mixture of 2.1 g (6 mmoles) of benzylpenicillin sulfoxide, 20 ml of chloroform, 20 ml (200 mmoles) of α-picoline, 8 ml (33 mmoles) of N,O-bis(trimethylsilyl)-acetamide and 1.6 ml (5.8 mmoles) of concentrated sulfuric acid was heated at 83° C to form the trimethylsilyl derivative of benzylpenicillin sulfoxide in situ. After 24 hours, the yield of Δ³-7-phenylacetamido-desacetoxycephalosporanic acid was 12% as estimated by microbiological assay using the method described in Example II.

b. The experiment described in (a) was repeated except that 6.4 ml (26 mmoles) of N,O-bis-(trimethylsilyl)acetamide and 1.14 g (6 mmoles) of p-toluenesulfonic acid were used instead of 1.16 ml of concentrated sulfuric acid to obtain a 15% yield of Δ³-7-phenylacetamido-desacetoxycephalosporanic acid after 24 hours heating at 83° C as estimated by microbiological assay using the method described in Example II.

c. The experiment described in (a) was repeated except that 5 ml (20 mmoles) of N,O-bis-(trimethylsilyl)acetamide and 2 ml of a 3.3 molar solution of α-picoline hydrochloride (6.6 mmoles) in dichloroethane were used instead of 1.6 ml of sulfuric acid. After heating for 24 hours at 85° C, the yield of Δ³-7-phenylacetamido-desacetoxycephalosporanic acid was 53% as estimated by microbiological assay using the method described in Example II.

EXAMPLE V

A mixture of 1.05 g (3 mmoles) of benzylpenicillin sulfoxide, 10 ml of benzyl cyanide, 10 ml (100 mmoles) of α-picoline, 3 ml of a 3.3 molar solution of α-picoline hydrochloride (10 mmoles) in 1,2-dichloroethane and 2.5 ml (10 mmoles) of N,O-bis(trimethylsilyl)-acetamide was heated at 95° C to form the trimethylsilyl derivative of benzylpenicillin sulfoxide in situ. After 6 hours of heating the yield of Δ³-7-phenylacetamido-desacetoxycephalosporanic acid was 48% as estimated by microbiological assay using the method described in Example II.

EXAMPLE VI

The experiment described in Example V was repeated except that 15 ml of benzyl cyanide and 5 ml (50 mmoles) of α-picoline were used to form the trimethylsilyl derivative of benzylpenicillin sulfoxide in situ. The yield of Δ³-7-phenylacetamido-desacetoxycephalosporanic acid after 6 hours heating at 95° C was 48% as estimated by microbiological assay using the method described in Example II.

EXAMPLE VII

The experiment described in Example V was repeated except that 17.5 ml of benzyl cyanide, 2.5 ml (25 mmoles) of α-picoline and 2 ml of a 3.3 molar solution of α-picoline hydrochloride (6.6 mmoles) in 1,2-dichloroethane were used to form the trimethylsilyl derivative of benzylpenicillin sulfoxide in situ. The yield of Δ³-7-phenylacetamido-desacetoxycephalosporanic acid after 6 hours heating at 95° C was 48% as estimated by microbiological assay using the method described in Example II.

EXAMPLE VIII

A mixture of 1 g (3 mmoles) of benzylpenicillin sulfoxide, 15 ml of benzyl cyanide, 7.2 ml (72 mmoles) of pyridine, 2.5 ml (10 mmoles) of N,O-bis(trimethylsilyl)-acetamide and 0.27 ml (1 mmole) of a 3.3 molar solution of α-picoline hydrochloride was heated at 90° C to form the trimethylsilyl derivative of benzylpenicillin sulfoxide in situ. After 6 hours of heating the yield of Δ³-7-phenylacetamido-desacetoxycephalosporanic acid was 38% as estimated by microbiological assay using the method described in Example II.

EXAMPLE IX

A mixture of 1.05 g (3 mmoles) of benzylpenicillin sulfoxide, 20 ml of benzyl cyanide, 2.5 ml (10 mmoles) of N,O-bis(trimethylsilyl)acetamide and 0.24 g (1.5 mmoles) of pyridine hydrobromide was heated at 90° C to form the trimethylsilyl derivative of benzylpenicillin sulfoxide in situ. After 10 hours of heating, the yield of $\Delta^3$-7-phenylacetamido-desacetoxycephalosporanic acid was 54% as estimated by microbiological assay.

EXAMPLE X

The procedure of Example IX was repeated using 0.48 g (3 mmoles) instead of 0.24 g of pyridine hydrobromide and with the addition of 0.3 ml (3 mmoles) of α-picoline to form the trimethylsilyl derivative of benzylpenicillin sulfoxide in situ. After heating for 10 hours at 90° C, the yield of $\Delta^3$-7-phenylacetamido-desacetoxycephalosporanic acid was 59% as estimated by microbiological assay.

EXAMPLE XI

A mixture of 1.05 g (3 mmoles) of benzylpenicillin sulfoxide, 20 ml of dioxane, 2.5 ml (10 mmoles) of N,O-bis(trimethylsilyl)acetamide, 0.48 g (3 mmoles) of pyridine hydrobromide and 0.3 ml (3 mmoles) of α-picoline was heated at 85° C to form the triemthylsilyl derivative of benzylpenicillin sulfoxide in situ. After 22 hours of heating, the reaction mixture was poured into 150 ml of a 0.75 molar potassium phosphate aqueous solution buffered to pH 7 and washed with 50 ml of chloroform. The pH of the aqueous layer was adjusted to 2 in the presence of 50 ml of ethyl acetate and the ethyl acetate layer was washed with water and dried over anhydrous sodium sulfate. Evaporation of the ethyl acetate gave 1 g of $\Delta^3$-7-phenylacetamido-desacetoxycephalosporanic acid with a purity of 56% as estimated by PMR, using 2,6-dichloroacetophenone as internal reference.

EXAMPLE XII

A mixture of 1.05 g (3 mmoles) of benzylpenicillin sulfoxide, 20 ml of dioxane, 2.5 ml (10 mmoles) of N,O-bis(trimethylsilyl)acetamide, 0.5 ml (3 mmoles) of a 6 molar solution of α-picoline hydrobromide in dichloromethane and 0.6 ml (6 mmoles) of α-picoline was heated at 102° C with stirring to form the trimethylsilyl derivative of benzylpenicillin sulfoxide in situ. After 6 hours, the reaction mixture was poured into a mixture of 200 ml of a 0.75 molar potassium phosphate aqueous solution buffered to pH 7 and 50 ml of ethyl acetate. The buffered aqueous layer was washed with 50 ml of ethyl acetate, and after adjustment of the pH to 2, the aqueous layer was extracted twice with 100 ml of ethyl acetate. After drying over magnesium sulfate, the ethyl acetate was evaporated under reduced pressure to obtain 1.07 g (yield 2.25 mmoles; 75%) of residue which contained 70% of $\Delta^3$-7-phenylacetamido-desacetoxycephalosporanic acid as estimated by U.V. and P.M.R.

EXAMPLE XIII 0.64 g (3.3 mmoles) of triethylbromosilane was added to a mixture of 1.05 g (3 mmoles) of benzylpenicillin sulfoxide, 20 ml of dioxane, and 0.9 ml (9 mmoles) of α-picoline. After stirring for half an hour, the triethylsilyl derivative of benzylpenicillin sulfoxide was formed in situ with its presence being confirmed by PMR. Then, 2.5 ml (10 mmoles) of N,O-bis(trimethylsilyl)acetamide were added and the mixture containing α-picoline hydrobromide was heated for 4 hours at 102° C. After treating the reaction mixture as described in Example II, the yield of $\Delta^3$-7-phenylacetamido-desacetoxycephalosporanic acid was 73% as estimated by microbiological assay.

EXAMPLE XIV a. To a mixture of 20 ml of a 0.15 molar solution of hydrogen chloride (3 mmoles) in dioxane and 2.5 ml (10.2 mmoles) of N,O-bis(trimethylsilyl)acetamide, there was added 1.05 g (3 mmoles) of benzylpenicillin sulfoxide to form the trimethylsilyl derivative of benzylpenicillin sulfoxide in situ. After refluxing for 6 hours at 102° C, the reaction mixture was treated as described in Example II to obtain a 10% yield of $\Delta^3$-7-phenylacetamido-desacetoxycephalosporanic acid as estimated by microbiological assay.

b. To a mixture of 2 ml (3 mmoles) of a 1.5 molar solution of hydrogen chloride in benzyl cyanide, 2.5 ml (10 mmoles) of N,O-bis(trimethylsilyl)acetamide and 0.9 ml (9 mmoles) of α-picoline in 19 ml of benzyl cyanide, there was added 1.05 g (3 mmoles) of benzylpenicillin sulfoxide. The mixture was heated at 95° C for 6 hours, and the yield of $\Delta^3$-7-phenylacetamido-desacetoxycephalosporanic acid formed was estimated by the method described in Example II to be 48%.

EXAMPLE XV a. To 1.05 g (3 mmoles) of benzylpenicillin sulfoxide there were added 18 ml of dioxane, 2.5 ml (10 mmoles) of N,O-bis-(trimethylsilyl)acetamide and 0.9 ml (9 mmol) of α-picoline and after a few minutes, 2 ml of a solution of 1.5 molar hydrogen bromide (3 mmoles) in dioxane was added thereto. The resulting mixture was heated for 6 hours at 101° C to form the trimethylsilyl derivative of benzylpenicillin sulfoxide in situ. Treatment of the reaction mixture as described in Example II gave a 97% yield of $\Delta^3$-7-phenylacetamido-desacetoxycephalosporanic acid as estimated by microbiological assay.

b. A mixture of 1.05 g (3 mmoles) of benzylpenicillin sulfoxide, 2.5 ml (10 mmoles) of N,O-bis(trimethylsilylacetamide, 0.3 ml (3 mmoles) of α-picoline and 0.25 ml (1.5 mmoles) of a 6 molar solution of α-picoline hydrogen bromide in 20 ml of dioxane was refluxed for 4.5 hours to form the trimethylsilyl derivative of benzylpenicillin sulfoxide in situ. The yield of $\Delta^3$-7-phenylacetamido-desacetoxycephalosporanic acid was 82% as estimated by microbiological assay.

c. The experiment described in (b) was repeated except that 0.9 ml (9 mmoles) instead of 0.3 ml of α-picoline and 420 mg (3 mmoles) of bromoacetic acid instead of α-picoline hydrogen bromide were used to form the trimethylsilyl derivative of benzylpenicillin sulfoxide in situ. The yield of $\Delta^3$-7-phenylacetamido-desacetoxycephalosporanic acid was 32% as estimated by microbiological assay.

d. The experiment described in (c) was repeated except that 700 mg (3 mmoles) of picric acid were used instead of bromoacetic acid to form the trimethylsilyl derivative of benzylpenicillin sulfoxide in situ. The yield of $\Delta^3$-7-phenylacetamido-desacetoxycephalosporanic acid was 47% as estimated by microbiological assay.

e. The experiment described in (c) was repeated except that 875 mg (3 mmoles) of tris(ethylsulfonyl)methane [$(C_2H_5SO_2)_3CH$] instead of bromoacetic acid were used to form the trimethylsilyl derivative of benzylpenicillin sulfoxide in situ. The yield of $\Delta^3$-7-phenylacetamido-desacetoxycephalosporanic acid was 28% as estimated by microbiological assay.

EXAMPLE XVI a. 530 mg (1.5 mmoles) of benzylpenicillin sulfoxide was suspended in 10 ml of dioxane and after the addition of 0.45 ml (4.5 mmoles) of α-picoline, the clear solution was cooled to 0° C. With vigorous stirring, 0.05 ml (0.5 mmoles) of phosphorous tribromide was added and the mixture was stirred for 30 minutes at 0° C to form the anhydride of benzylpenicillin sulfoxide and phosphorus tribromide in situ. Then, 0.9 ml (3.5 mmoles) of N,O-bis(trimethylsilyl)acetamide was added and after 4.5 hours of refluxing, the amount of $\Delta^3$-7-phenylacetamido-desacetoxycephalosporanic acid formed was 85% as estimated by microbiological assay.

b. The experiment described in (a) was repeated except that 0.05 ml (0.5 mmoles) of acetyl bromide was used instead of phosphorus tribromide and the intermediate product formed was in this case the acetyl anhydride of benzylpenicillin sulfoxide. The yield of $\Delta^3$-7-phenylacetamido-desacetoxycephalosporanic acid was 87% as estimated by microbiological assay.

c. The experiment described in (b) was repeated except that the acetyl bromide was added while the mixture was at room temperature. The yield was 83% of $\Delta^3$-7-phenylacetamido-desacetoxycephalosporanic acid as estimated by microbiological assay.

d. The experiment described in (b) was repeated except that 0.36 ml (4.5 mmoles) of pyridine was used instead of α-picoline and yield of $\Delta^3$-7-phenylacetamido-desacetoxycephalosporanic acid was 94%.

e. The experiment described in (d) was repeated except that 0.07 ml (1.0 mmole) instead of 0.05 ml of acetyl bromide was used and the yield of $\Delta^3$-7-phenylacetamido-desacetoxycephalosporanic acid was 92%.

f. The experiment described in (d) was repeated except that 0.14 ml (2.0 mmoles) instead of 0.05 ml of acetyl bromide was used and the yield of $\Delta^3$-7-phenylacetamido-desactoxycephalosporanic acid was 93%.

g. The experiment described in (d) was repeated except that 0.05 ml of oxalyl bromide was used instead of acetyl bromide and the intermediate product formed was in this case the oxalyl anhydride of benzylpenicillin sulfoxide. The yield of $\Delta^3$-7-phenylacetamido-desacetoxycephalosporanic acid was 69%.

h. The experiment described in (e) was repeated except that 10 ml of toluene were used as the solvent instead of dioxane and the acetyl anhydride of benzylpenicillin sulfoxide was formed in situ. The yield of $\Delta^3$-7-phenylacetamido-desacetoxycephalosporanic acid was 76%.

i. The experiment described in (e) was repeated except that 10 ml of butyl acetate were used instead of dioxane and the yield of $\Delta^3$-7-phenylacetamido-desacetoxycephalosporanic acid was 78%.

EXAMPLE XVII

A solution of 10.5 g (30 mmoles) of benzylpenicillin sulfoxide in 150 ml of dioxane and 7.2 ml (90 mmoles) of pyridine was cooled to 6° C. After the addition of a solution of 1.4 ml (18.5 mmoles) of acetyl bromide in 50 ml of dioxane, the mixture was stirred for 30 minutes at 5° C to form the acetyl anhydride of benzylpenicillin sulfoxide in situ. Then, 18 ml (70 mmoles) of N,O-bis(trimethylsilyl)acetamide were added and the reaction mixture was refluxed for 4.5 hours. After cooling, the mixture was poured into 1 l. of a 0.2 molar potassium phosphate aqueous solution buffered to pH 7. After adjustment of the pH to 7 with 4N potassium hydroxide solution, 600 ml of butyl acetate were added thereto. The mixture was shaken and afterwards the two layers were allowed to separate in a separating funnel. The aqueous layer was washed with 400 ml of butyl acetate and the combined butyl acetate layers were extracted with 500 ml of a 0.75 molar potassium phosphate aqueous solution buffered to pH 7 and the extract added to the main aqueous solution. The combined aqueous solution contained 9.1 g of the potassium salt of $\Delta^3$-7-phenylacetamido-desacetoxycephalosporanic acid (yield 82%) as estimated by U.V. and by microbiological assay using Escherichia coli as the test microorganism. The potassium salt of $\Delta^3$-7-phenylacetamido-desacetoxycephalosporanic acid was isolated as in Example I to obtain 11.1 g (75% yield) of product with a purity of 67% as estimated by microbiological assay.

EXAMPLE XVIII a. 530 mg (1.5 mmoles) of benzylpenicillin sulfoxide were suspended in 10 ml of dioxane and after the addition of 0.45 ml (4.5 mmoles) of α-picoline, the clear solution was cooled to 0° C. With vigorous stirring, 0.05 ml (0.7 mmoles) of acetyl bromide were introduced and the mixture was stirred for 30 minutes at 0° C to form the acetyl anhydride of benzylpenicillin sulfoxide in situ. Then, 1.35 g (6.6 mmoles) of N,N'-bis(trimethylsilyl)urea were added and, after 4.5 hours of refluxing, the amount of $\Delta^3$-7-phenylacetamido-desacetoxycephalosporanic acid was estimated by microbiological assay to be 54%.

b. The experiment described in (a) was repeated except that 0.05 ml (0.5 mmoles) of phosphorus tribromide was used instead of acetyl bromide and the intermediate product formed was the anhydride of benzylpenicillin sulfoxide and phosphorus tribromide. The yield of $\Delta^3$-7-phenylacetamido-desacetoxycephalosporanic acid was 33% as estimated by microbiological assay.

c. The experiment described in (a) was repeated except that 10 ml of butyl acetate instead of dioxane and 0.12 ml (1.5 mmoles) of acetyl bromide instead of 0.7 mmoles were used and the yield of $\Delta^3$-7-phenylacetamido-desacetoxycephalosporanic acid was 54%.

d. The experiment described in (a) was repeated except that 0.36 ml (4.5 mmoles) of pyridine instead of α-picoline and 0.22 ml (2.5 mmoles) of trimethylbromosilane instead of acetyl bromide were used and the intermediate product formed was the trimethylsilyl derivative of benzylpenicillin sulfoxide. The yield of $\Delta^3$-7-phenylacetamido-desacetoxycephalosporanic acid was 80%.

e. 525 mg (1.5 mmoles) of benzylpenicillin sulfoxide and 760 mg (3.7 mmoles) of N,N'-bis(trimethylsilyl)urea were suspended in 10 ml of toluene and then, 0.12 ml (1.5 mmoles) of pyridine and 0.12 ml (1.0 mmole) of benzoyl bromide were added and the mixture was heated at 100° C. for 5 hours to form the benzoyl anhydride of benzylpenicillin sulfoxide as an intermediate. The yield of $\Delta^3$-7-phenylacetamido-desacetoxycephalosporanic acid was 57% as estimated by microbiological assay.

f. The experiment described in (e) was repeated except that several other acid derivatives were used instead of benzoyl bromide. The results are summarized in Table I.

TABLE I

| Acid derivative | Amount of acid derivative used (mmoles) | % Yield of $\Delta^3$-7-phenylacetamido-desacetoxy-cephalosporanic acid |
|---|---|---|
| 1. Trichloroacetyl bromide | 1.0 | 67 |
| 2. Trichloroacetyl chloride | 1.0 | 67 |
| 3. Propionyl bromide | 1.0 | 75 |
| 4. Phosgene | 0.5 | 31 |
| 5. Thionyl chloride | 0.55 | 32 |
| 6. Thionyl bromide | 0.65 | 67 |
| 7. p-Tolylsulfonyl chloride | 1.0 | 21 |
| 8. Boron tribromide | 0.37 | 81 |
| 9. Aluminium tribromide | 0.34 | 40 |
| 10. Silicon tetrabromide | 0.25 | 73 |
| 11. Germanium tetrabromide | 0.25 | 82 |
| 12. Tin tetrabromide | 0.25 | 26 |
| 13. Phosphorus pentabromide | 0.2 | 82 |
| 14. Phosphorus oxybromide | 0.33 | 75 |
| 15. Phosphorus thiobromide | 0.37 | 74 |
| 16. Tungsten pentabromide | 0.2 | 56 |

It is understood that the trichloroacetyl (1, 2), propionyl (3), carbonyl (4), thionyl (5, 6), p-tolysulfonyl (7), anhydride of benzylpenicillin sulfoxide and the anhydride of benzylpenicillin sulfoxide and boron tribromide (8), aluminum tribromide (9), silicon tetrabromide (10), germanium tetrabromide (11), tin tetrabromide (12), phosphorus pentabromide (13), phosphorus oxybromide (14), phosphorus thiobromide (15), and tungsten pentabromide (16), were formed as intermediate products.

EXAMPLE XIX 525 mg (1.5 mmoles) of benzylpenicillin sulfoxide and 1.4 g (7 mmoles) of N,N'-bis(trimethylsilyl)urea were suspended in 10 ml of dioxane and 0.35 ml (2 mmoles) of a 6 molar solution of α-picoline hydrobromide in dichloromethane were added and the mixture was heated at 100° C for 4 hours to form the trimethylsilyl derivative of benzylpenicillin sulfoxide in situ. The amount of $\Delta^3$-7-phenylacetamido-desacetoxycephalosporanic acid formed was estimated at 80% using the method described in Example II.

EXAMPLE XX a. 525 mg (1.5 mmoles) of benzylpenicillin sulfoxide and 1.05 g (5 mmoles) of N,N'-bis (trimethylsilyl)urea were suspended in 10 ml of dioxane and 0.25 ml (3 mmoles) of pyridine and 0.15 ml (1.6 mmoles) of trimethylbromosilane were added and the mixture heated at 100° C for 4.5 hours to form the trimethylsilyl derivative of benzylpenicillin sulfoxide in situ. The amount of $\Delta^3$-7-phenylacetamido-desacetoxycephalosporanic acid formed was 85% as estimated by microbiological assay.

b. The experiment described in (a) was repeated except that 0.16 ml (1.6 mmoles) of α-picoline was used instead of pyridine to obtain a yield of 85%.

c. The experiment described in (a) was repeated except that 0.83 ml (3.4 mmoles) of N,O-bis(trimethylsilyl)acetamide was used instead of N,N'-bis(trimethylsilyl)urea and the yield of $\Delta^3$-7-phenylacetamido-desacetoxycephalosporanic acid was 69% as estimated by microbiological assay.

EXAMPLE XXI 525 mg (1.5 mmoles) of benzylpenicillin sulfoxide and 1.05 g (5 mmoles) of N,N'-bis(trimethylsilyl)urea were suspended in 10 ml of butyl acetate and 0.23 ml (2.3 mmoles) of α-picoline and 0.2 ml (2.2 mmoles) of trimethylbromosilane were added to form the trimethylsilyl derivative of benzylpenicillin sulfoxide in situ. After heating at 100° C for 4.5 hours, the yield of $\Delta^3$-7-phenylacetamido-desacetoxycephalosporanic acid was 78% as estimated by microbiological assay.

EXAMPLE XXII

A mixture of 1.05 g (3 mmoles) of benzylpenicillin sulfoxide, 3.1 ml (15 mmoles) of hexamethyldisilazane, 6 ml of a 0.5 molar solution of hydrogen bromide in dioxane and 14 ml of dioxane was heated at 100° C for 4.5 hours to form the trimethylsilyl derivative of benzylpenicillin sulfoxide in situ. The yield of $\Delta^3$-7-phenylacetamido-desacetoxycephalosporanic acid formed was estimated by the method described in Example II to be 48%.

EXAMPLE XXIII a. A mixture of 1.05 g (3 mmoles) of benzylpenicillin sulfoxide, 18 ml of dioxane 0.9 ml (9 mmoles) of α-picoline, 2.6 g (10 mmoles) of N,O-bis(trimethylsilyl)-trifluoroacetamide and 2 ml of a 1.5 molar solution of hydrogen bromide in dioxane was refluxed for 4.5 hours to form the trimethylsilyl derivative of benzylpenicillin sulfoxide in situ. The yield of $\Delta^3$-7-phenylacetamido-desacetoxycephalosporanic acid formed was estimated by microbiological assay to be 73%.

b. The experiment described in (a) was repeated except that 1.8 (10 mmol) of N,N'-bis(trimethylsilyl)-carbodiimide was used instead of N,O-bis(trimethylsilyl)trifluoroacetamide to form the trimethylsilyl derivative of benzylpenicillin sulfoxide in situ. The yield of $\Delta^3$-7-phenylacetamido-desacetoxycephalosporanic acid was 14% as estimated by microbiological assay.

EXAMPLE XXIV 1.05 g (3 mmoles) of benzylpenicillin sulfoxide was suspended in 15 ml of dioxane and 2.5 ml (10 mmoles) of N,O-bis(trimethylsilyl)acetamide, 1.2 ml (9 mmoles) of 2-methylquinoline and 6 ml of a 0.5 molar solution of hydrogen bromide in dioxane were added thereto and the mixture heated at 100° C for 4.5 hours to form the trimethylsilyl derivative of benzylpenicillin sulfoxide in situ. The amount of $\Delta^3$-7-phenylacetamido-desacetoxycephalosporanic acid form was estimated by the method described in Example II by microbiological assay using *Escherichia coli* as the test microorganism to be 49%.

The experiment was repeated using several bases other than 2-methylquinoline and the results are summarized in Table II.

TABLE II

| Base | Amount of base (mmole) | % Yield of $\Delta^3$-7-phenylacetamido-desacetoxycephalosporanic acid |
|---|---|---|
| 1. diphenylamine | 3 | 54 |
| 2. aniline | 9 | 58 |
| 3. N-methylaniline | 9 | 53 |
| 4. hexamethylenetetraamine | 2.25 | 73 |
| 5. 3-methylpyridine | 9 | 75 |

TABLE II-continued

| Base | Amount of base (mmole) | % Yield of Δ³-7-phenylacetamido-desacetoxycephalosporanic acid |
|---|---|---|
| 6. 4-methylpyridine | 9 | 82 |
| 7. 2,3-dimethylpyridine | 9 | 80 |
| 8. 2,6-dimethylpyridine | 9 | 52 |
| 9. 2-ethylpyridine | 9 | 68 |
| 10. 2-propylpyridine | 9 | 85 |
| 11. 4-benzylpyridine | 9 | 75 |
| 12. 4-phenylpyridine | 9 | 81 |
| 13. 2-dimethylamino-pyridine | 9 | 84 |
| 14. 1,3,5-collidine | 9 | 84 |
| 15. quinoline | 9 | 84 |
| 16. isoquinoline | 9 | 89 |
| 17. 3-methyl-iso-quinoline | 9 | 72 |
| 18. pyrazole | 9 | 54 |
| 19. imidazole | 3 | 69 |
| 20. N-methylimidazole | 3 | 87 |

EXAMPLE XXV a. A mixture of 525 mg (1.5 mmoles) of benzylpenicillin sulfoxide, 10 ml of toluene, 0.12 ml (1.5 mmoles) of pyridine, 1.45 ml (9 mmoles) of N-methyl-N-trimethylsilyl-acetamide and 0.35 ml of a 6 molar solution of α-picoline hydrobromide in dichloromethane was heated at 100° C for 5 hours to form the trimethylsilyl derivative of benzylpenicillin sulfoxide in situ. The yield of Δ³-7-phenylacetamido-desacetoxycephalosporanic acid formed was 58% as estimated by microbiological assay.

b. The previous experiment was repeated except that 1.7 ml (9.2 mmoles) of N-methyl-N-trimethylsilyl-trifluoroacetamide were used instead of the N-methyl-N-trimethylsilylacetamide and the yield of Δ³-7phenylacetamido-desacetoxycephalosporanic acid was 86%.

EXAMPLE XXVI

A mixture of 1.05 g (3 mmoles) of benzylpenicillin sulfoxide, 2.5 ml (10 mmoles) of N,O-bis(trimethylsilyl)-acetamide, 0.6 ml(6 mmoles ofα-picoline and 0.5 ml of a 6 molar solution of α-picoline hydrobromide in methylene chloride in 20 ml of dioxane was refluxed for 4.5 hours to form the trimethylsilyl derivative of benzylpenicillin sulfoxide in situ. The amount of Δ³-7-phenylacetamido-desacetoxycephalosporanic acid was estimated as described in Example II by microbiological assay to be 82%.

The experiment was repeated using solvents other than dioxane and the results are summarized in Table III.

TABLE III

| Solvent | % Yield of Δ³-7-phenylacetamido-desacetoxycephalosporanic acid |
|---|---|
| 1,2,3-trichloropropane | 40 |
| toluene | 41 |
| N,N-dimethylacetamide | 44 |
| diethylmethylsulfonamide | 49 |
| chlorobenzene | 52 |
| isoamyl acetate | 60 |
| butyl acetate | 64 |
| diethyl oxalate | 82 |
| anisole | 81 |
| 1,2-dimethoxyethane | 58 |
| tetraethylene glycol dimethyl ether | 81 |
| triethylene glycol dimethyl ether | 64 |

EXAMPLE XXVII 1.3 g (3 mmoles) of 2-ethoxynaphthylpenicillin sulfoxide, 2.5 ml (10 mmoles) of N,O-bis(trimethylsilyl)acetamide, 0.3 ml (3 mmoles) of α-picoline and 0.25 ml (1.5 mmoles) of a 6 molar solution of α-picoline hydrobromide in methylene chloride were dissolved in 20 ml of dioxane to form the trimethylsilyl derivative of 2-ethoxynaphthylpenicillin sulfoxide in situ. The mixture was refluxed for 4.5 hours and then poured into a cold mixture of 200 ml of a 0.75 molar potassium phosphate aqueous solution buffered to pH 7 and 50 ml of ethyl acetate. After adjustment of the pH to 7 with 4N potassium hydroxide solution, the mixture was transferred into a separating funnel, shaken and allowed to stand. The aqueous layer was washed with 50 ml of ethyl acetate and, after adjustment of the pH to 2 with a 4N sulfuric acid solution was extracted twice with 100 ml of ethyl acetate. After drying over magnesium sulfate, the ethyl acetate was evaporated under reduced pressure and the dried residue of 490 mg contained 80% of Δ³-7-(2-ethoxynaphthamido)-desacetoxycephalosporanic acid as estimated by PMR, using 2,6-dichloroacetophenone as an internal reference. The yield was 31%.

EXAMPLE XXVIII

The experiment described in Example XXVII was repeated with 1.1 g (3 mmoles) of phthalimidopenicillin sulfoxide except that 0.25 ml of α-picoline hydrobromide solution and 0.3 ml α-picoline were replaced by 0.5 ml (3 mmoles) of a 6 molar solution of α-picoline hydrobromide in methylene chloride to form the trimethylsilyl derivative of phthalimido-penicillin sulfoxide in situ. The reaction mixture was treated in the same manner as described in Example XXVII to obtain 880 mg (72% yield) of Δ³-7-phthalimido-desacetoxycephalosporanic acid with a purity of 84%.

EXAMPLE XXIX

The experiment described in Example XXVII was repeated with 1.3 g (3 mmoles) of benzenesulfonamido-methylpenicillin sulfoxide to obtain the trimethylsilyl derivative of benzenesulfonamidomethylpenicillin sulfoxide in situ. 1.3 g (66% yield) of Δ³-7-benzenesulfonamidomethyl-desacetoxycephalosporanic acid with a purity of 63% was obtained.

EXAMPLE XXX a. To 1.1 g (3 mmoles) of phenoxymethylpenicillin sulfoxide were added 20 ml of dioxane, 2.5 ml (10 mmoles) of N,O-bis(trimethylsilyl)acetamide, 0.6 ml of α-picoline (6 mmoles) and a 0.5 ml (3 mmoles) of 6 molar solution of α-picoline hydrobromide in methylene chloride to form the trimethylsilyl derivative of phenoxymethylpenicillin sulfoxide in situ. The mixture was refluxed for 4.5 hours and then treated as described in Example II. The yield of Δ³-7-phenoxyacetamido-desacetoxycephalosporanic acid was 71% as estimated by a direct microbiological assay using *Escherichia coli* as the test microorganism.

b. The experiment described in (a) was repeated except that the reaction mixture was worked up as described in Example XXVII, resulting in 860 mg (70% yield) of $\Delta^3$-7-phenoxyacetamido-desacetoxycephalosporanic acid of a purity of 85%, as estimated by its PMR spectrum, using 2,6-dichloro-acetophenone as an internal reference.

EXAMPLE XXXI

To a suspension of 1.35 g (3 mmoles) of the cyclohexylammonium salt of benzylpenicillin sulfoxide in 15 ml of dioxane was added 2.8 ml (11 mmoles) of N,O-bis(trimethylsilyl)acetamide and 6 ml of a 0.5 molar solution of hydrogen bromide in dioxane to form the trimethylsilyl derivative of benzylpenicillin sulfoxide in situ. The mixture was refluxed for 4.5 hours and the yield of $\Delta^3$-7-phenylacetamido-desacetoxycephalosporanic acid was estimated to be 55% by microbiological assay.

EXAMPLE XXXII

PREPARATION OF THE MIXED ANHYDRIDE OF PHENOXYMETHYLPENICILLIN SULFOXIDE AND ACETIC ACID a. A solution of 0.28 ml (3 mmoles) of acetyl bromide in 5 ml of 1,2-dichloroethane was added to a solution of 1.1 g (3 mmoles) of phenoxymethylpenicillin sulfoxide and 0.72 ml (9 mmoles) of pyridine in 20 ml of 1,2-dichloroethane. After stirring for 1 hour at 0° C, the mixture was filtered and evaporated to dryness. The residual form of 1.08 g (2.6 mmoles) was the mixed anhydride of phenoxymethylpenicillin sulfoxide and acetic acid.

Analysis of the IR spectrum: (in CHCl$_3$): 1820; 1800 and 1758 cm$^{-1}$.

Analysis of the PMR spectrum (in CDCl$_3$), δ: 1.35 (s, 3); 1.74 (s, 3); 2.32 (s, 3); 4.55 (s, 2); 4.67 (s, 1); 5.17 (d, 1, J= 4.5 Hz); 6.12 (q, 1, J = 11 Hz and J = 4.5 Hz); 6.98 (s, 5).

b. 2.2 g (5 mmoles) of the anhydride of phenoxymethylpenicillin sulfoxide and acetic acid was dissolved in 30 ml of dioxane and after adding 3 ml (11.7 mmoles) of N,O-bis(trimethylsilyl)acetamide, 1.1 ml (15 mmoles) of pyridine and 0.6 ml of dichloromethane containing 3.6 mmoles of α-picoline hydrobromide, the mixture was heated to reflux for 4.5 hours. The reaction mixture was cooled to room temperature and poured into a stirred mixture of 400 ml of a 0.75 molar potassium phosphate aqueous solution buffered to pH 7 and 100 ml of ethyl acetate. After adjusting the pH to 7 with 4N potassium hydroxide, the mixture was transferred to a separating funnel, shaken and allowed to stand. The aqueous layer was separated, washed with 100 ml of ethyl acetate and, after adjusting the pH to 2 with a 4N sulfuric acid solution, twice extracted with 200 ml of ethyl acetate. After drying the reaction mixture over anhydrous magnesium sulfate, the ethyl acetate was evaporated under reduced pressure to obtain a residue of 1.28 g (63% yield) contained 86% of $\Delta^3$-7-phenoxyacetamido-desacetoxycephalosporanic acid as estimated by its PMR spectrum, using 2,6-dichloroacetophenone as an internal reference.

This example shows that the anhydride which is formed as an intermediate may be separated from the reaction mixture, and, as in the case where the anhydride is formed in situ, may be used for ring enlargement.

EXAMPLE XXXIII

A mixture of 1.05 g (3 mmoles) of benzylpenicillin sulfoxide, 0.9 ml (9 mmoles) of α-picoline and a solution of 3.0 mmoles of hydrogen bromide in dioxane was refluxed for 4.5 hours with different amounts of N,O-bis(trimethylsilyl)acetamide as specified in the following Table. (The total volume was always 2.4 ml). The yield of $\Delta^3$-7-phenylacetamidodesacetoxycephalosporanic acid was estimated by microbiological assay, and the results are indicated in the Table.

| Amount of N,O-bis)tri-methylsilyl)acetamide used (mmoles) | % Yield of $\Delta^3$-7-phenylacetamido-desacetoxycephalosporanic acid |
|---|---|
| 4.5 | 0 |
| 6 | 56 |
| 7.5 | 82 |
| 9 | 85 |
| 10 | 85 |
| 12.5 | 70 |
| 15 | 46 |
| 20 | 21 |
| 40 | 0 |

The table shows that the highest yield under the above-mentioned circumstances was 85% and was obtained with an amount of about 9 to 10 mmoles of N,O-bis(trimethylsilyl)acetamide.

Various modifications of the products and process of the invention may be made without departing from the spirit or scope thereof and it should be understood that the invention is intended to be limited only as defined in the appended claims.

We claim:

1. A process for the preparation of 7β-acylamido-3-methyl-3-cephem-4-carboxylic acids by conversion of the corresponding 6β-acylamido penicillanic sulfoxide acids comprising heating a 6β-acylamidopenicillanic sulfoxide acid anhydride having the group —COOR$_3$, selected from the group consisting of a. an acid anhydride group wherein R$_3$ is

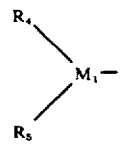

wherein R$_4$ and R$_5$ are the same or different and each is selected from the group consisting of lower alkyl of 1 to 6 carbon atoms, cycloalkyl of 5 to 8 carbon atoms, phenyl, phenyl alkyl having 1 to 2 carbon atoms in the alkyl, lower alkoxy and lower alkylthio of 1 to 6 carbon atoms, phenoxy, phenylalkoxy containing 1 to 2 carbon atoms in the alkoxy, halogen and a 6β-acylamido-penicillanylsulfoxide-3-carbonyloxy group, or R$_4$ and R$_5$ together form an alkylene group and M$_1$ is selected from the group consisting of boron, aluminum and phosphorous atoms and b. an acid anhydride group wherein R$_3$ has the formula

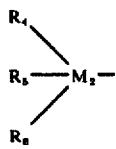

VI wherein $R_4$, $R_5$ and $R_6$ are the same or different and each is selected from the group consisting of lower alkyl of 1 to 6 carbon atoms, cycloalkyl of 5 to 8 carbon atoms, phenyl, phenylalkyl having 1 to 2 carbon atoms in the alkyl, lower alkoxy of 1 to 6 carbon atoms, lower alkylthio of 1 to 6 carbon atoms, phenoxy, phenylalkoxy group having 1 to 2 carbon atoms in the alkoxy, halogen and a 6β-acylamidopenicillanyl sulfoxide-3-carbonyloxy group or $R_4$ and $R_5$ together form an alkylene group or $R_4$ and $R_5$ or $R_6$ together are selected from the group consisting of =O and =S, and $M_2$ is selected from the group consisting of silicon, sulfur, germanium and tin atoms, or a carbon atom when $R_4$ and $R_6$ together are selected from the group consisting of =O and =S.

c. an acid anhydride group wherein $R_3$ has the formula

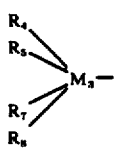

VII wherein $R_4$ and $R_5$ are the same or different and have the above definition, and $R_7$ and $R_8$ are the same or different and are selected from the group consisting of halogen and a 6β-acylamido-penicillanyl sulfoxide-3-carbonyloxy group or $R_7$ and $R_8$ together form an alkylene group or together are selected from the group consisting of =S and =O, and $M_3$ is selected from the group consisting of phosphorous and tungsten atoms, d. an acid anhydride group, wherein $R_3$ has the formula

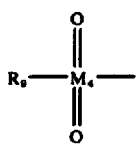

VIII wherein $R_9$ is selected from the group consisting of lower alkyl of 1 to 6 carbon atoms, cycloalkyl of 5 to 8 carbon atoms, phenyl, phenylalkyl having 1 to 2 carbon atoms in the alkyl, lower alkoxy of 1 to 6 carbon atoms, lower alkylthio of 1 to 6 carbon atoms, phenoxy, or phenylalkoxy group having 1 to 2 carbon atoms in the alkoxy, and $M_4$ is a sulfur atom and e. a group wherein $R_3$ is selected from the group consisting of an alkali metal, alkaline earth metal ion and a cation derived from an amine in a dry inert organic solvent at a temperature up to 160° C with an anhydrous acid capable of causing ring expansion of the penam ring to a Δ³-cephem ring in the presence of at least one molar equivalent based on the compound of a silicon-containing compound having a formula selected from the group consisting of

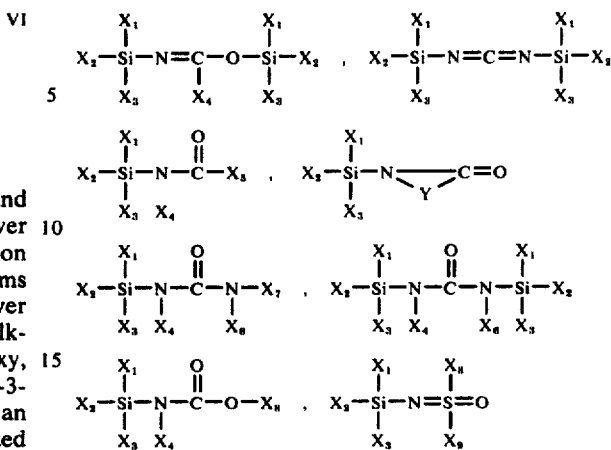

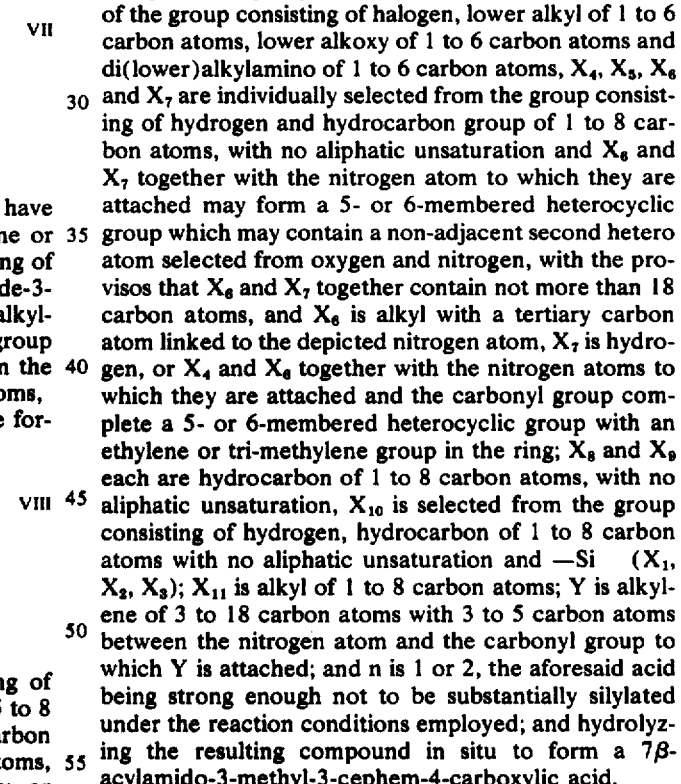

wherein $X_1$, $X_2$ and $X_3$ are individually selected from the group consisting of halogen, lower alkyl of 1 to 6 carbon atoms, lower alkoxy of 1 to 6 carbon atoms, phenyl, phenylalkyl of 1 to 2 alkyl carbon atoms, cycloalkyl of 5 to 8 carbon atoms and when the X's are not halogen or alkyl, optionally substituted with a member of the group consisting of halogen, lower alkyl of 1 to 6 carbon atoms, lower alkoxy of 1 to 6 carbon atoms and di(lower)alkylamino of 1 to 6 carbon atoms, $X_4$, $X_5$, $X_6$ and $X_7$ are individually selected from the group consisting of hydrogen and hydrocarbon group of 1 to 8 carbon atoms, with no aliphatic unsaturation and $X_6$ and $X_7$ together with the nitrogen atom to which they are attached may form a 5- or 6-membered heterocyclic group which may contain a non-adjacent second hetero atom selected from oxygen and nitrogen, with the provisos that $X_6$ and $X_7$ together contain not more than 18 carbon atoms, and $X_6$ is alkyl with a tertiary carbon atom linked to the depicted nitrogen atom, $X_7$ is hydrogen, or $X_4$ and $X_6$ together with the nitrogen atoms to which they are attached and the carbonyl group complete a 5- or 6-membered heterocyclic group with an ethylene or tri-methylene group in the ring; $X_8$ and $X_9$ each are hydrocarbon of 1 to 8 carbon atoms, with no aliphatic unsaturation, $X_{10}$ is selected from the group consisting of hydrogen, hydrocarbon of 1 to 8 carbon atoms with no aliphatic unsaturation and —Si ($X_1$, $X_2$, $X_3$); $X_{11}$ is alkyl of 1 to 8 carbon atoms; Y is alkylene of 3 to 18 carbon atoms with 3 to 5 carbon atoms between the nitrogen atom and the carbonyl group to which Y is attached; and n is 1 or 2, the aforesaid acid being strong enough not to be substantially silylated under the reaction conditions employed; and hydrolyzing the resulting compound in situ to form a 7β-acylamido-3-methyl-3-cephem-4-carboxylic acid.

2. The process of claim 1 wherein the said 7β-acylamido-3-methyl-3-cephem-4-carboxylic acid is reacted with a base to form the corresponding alkali metal, alkaline earth metal or amine salt.

3. The process of claim 1 employed during ring enlargement wherein the temperature is between 50° and 160° C.

4. The process of claim 1 wherein the temperature employed during ring enlargement is between 60° and 130° C.

5. The process of claim 1 wherein the phenyl in the definitions of $R_4$, $R_5$, $R_6$ and $R_9$ have a substituent selected from the group consisting of halogen, lower alkyl, lower alkoxy and di(lower)alkylamino.

6. The process of claim 1 wherein the group -COOR₃ is an acid anhydride group wherein R₃ is

7. The process of claim 1 wherein the group —COOR₃ is an acid anhydride group wherein R₃ is

8. The process of claim 7 wherein R₃ is

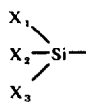

wherein $X_1$, $X_2$ and $X_3$ are individually selected from the group consisting of halogen, lower alkyl, lower alkoxy, phenylalkyl of 1 to 2 alkyl carbon atoms, cycloalkyl of 5 to 8 carbon atoms and a 6-acylamidopenicillanyl sulfoxide-3-carbonyloxy, the groups $X_1$, $X_2$ and $X_3$ when not halogen or alkyl being optionally substituted with a member of the group consisting of halogen, lower alkyl, lower alkoxy and di(lower)alkylamino.

9. The process of claim 8 wherein $X_1$, $X_2$ and $X_3$ are lower alkyl.

10. The process of claim 8 wherein $X_1$, $X_2$ and $X_3$ are methyl.

11. The process of claim 1 wherein the starting 6-acylamido penicillanic acid sulfoxide is reacted with a reagent of formulae V, VI, VII and VIII having its free bond attached to a halogen.

12. The process of claim 11 wherein the reagent is selected from the group consisting of $BBr_3$, $AlBr_3$, $PBr_3$, $(CH_3)_3SiBr$, $(C_2H_5)_3SiBr$, $COCl_2$, $CH_3COBr$, $BrCOCOBr$, $C_6H_5COBr$, $Cl_3CCOCl$, $Cl_3CCOBr$, $C_2H_5COBr$, $SOCl_2$, $SOBr_2$, $SiBr_4$, $GeBr_4$, $SnBr_4PBr_5$, $POBr_3$, $PSBr_3$, $WBr_5$ and $CH_3C_6H_4SO_2Cl$.

13. The process of claim 1 wherein the silicon compound is selected from the group consisting of N,O-bis(trimethylsilyl)acetamide, N,O,-bis(trimethylsilyl)-trifluoroacetamide N,N-bis(trimethylsilyl)-carbodiimide, N-(trimethylsilyl)-acetamide, N-methyl-N-(trimethylsilyl)-acetamide, N-methyl-N-(trimethylsilyl)-formamide, N-(trimethylsilyl)-2-pyrrolidone, N-(triethylsilyl)-urea, N,N'-bis(trimethylsilyl)urea, N-(triphenylsilyl)-ethylcarbamate, trimethylsilyldimethylsulfoxide, N-trimethylsilyl-N-methyl-trifluoroacetamide and trimethylsilylimidazole.

14. The process of claim 1 wherein the silicon compound is selected from the group consisting of trimethylsilylamine, N-ethyltriethylsilylamine, N-(trimethylsilyl)-diethylamine, hexamethyldisilazane, hexamethylcyclotrisilazane and octamethyl cyclotetrasilazane.

15. The process of claim 1 wherein the silicon-containing compound is selected from the group consisting of N,O-bis(trimethylsilyl)-acetamide and N,N'-bis(-trimethylsilyl) urea.

16. The process of claim 1 wherein the amount of silicon-containing compound used is at least one and a half molecular equivalent per mole of penicillanic acid sulfoxide.

17. The process of claim 16 wherein the amount of silicon-containing compound used is 2 to 4 molecular equivalent per mole of penicillin sulfoxide.

18. The process of claim 16 wherein the acid capable of causing ring expansion is selected from the group consisting of hydrogen bromide, hydrogen chloride, toluene-p-sulfonic acid, concentrated sulfuric acid, hydrogen iodide, perchloric acid, periodic acid, nitric acid, chloric acid, iodic acid, selenic acid, halogenated acetic acids, halogenated lower alkyl sulfonic acids, naphthalenesulfonic acid, oxalic acid, picric acid, tris-(ethylsulfonyl)-methane, pentacyanopropane, tetracyanopropene, pentacyanocyclopentadiene, tetracyanocyclopentadiene and tricyanocyclopentadiene and dinitroacetonitrile.

19. The process of claim 18 wherein the acid is hydrogen bromide.

20. The process of claim 18 wherein the acid is incorporated into the reaction as a complex with a nitrogen-containing base forming an acid addition salt complex.

21. The process of claim 20 wherein the base is selected from the group consisting of pyridine, a substituted pyridine, quinoline, a substituted quinoline, imidazole and a substituted imidazole.

22. The process of claim 21 wherein an excess of up to 10 moles per mol of acid of the nitrogen-containing base is employed in relation to the amount of acid.

23. The process of claim 20 wherein the nitrogen-containing bases are soluble in the organic solvent employed and have a pKa between 4 and 10.

24. The process of claim 1 wherein the molecular proportions of the substances included in the reaction mixture in relation to each mole of 6-acylamidopenicillanic acid sulfoxide employed are ¼ to 4 moles of acid, ¼ to 4 equivalents of carboxylic protecting reagent and at least 2 equivalents of silicon-containing compound.

25. The process of claim 1 wherein the dry inert organic solvent used is selected from the group consisting of acetonitrile, chlorobenzene, toluene, diethylmethylsulfonamide, dimethylformamide, N,N-dimethylacetamide, 1,2-dimethoxyethane, dioxane, triethyleneglycol, diethyl ether, tetraethyleneglycol diethyl ether, nitrobenzene, benzylcyanide, butyl acetate, isoamylacetate, diethyloxalate, anisole, benzene, carbon tetrachloride, dimethylsulfoxide, methyl ethyl ketone, methyl or ethyl isobutyl ketone, 1,2-dichloroethane, 1,1-dichloroethane, 1-bromo-1-chloroethane, 1,2,3-trichloropropane, methylenechloride and chloroform.

26. The process of claim 25 wherein the dry organic inert solvent is dioxane.

* * * * *

UNITED STATES PATENT OFFICE
CERTIFICATE OF CORRECTION
Page 1 of 3

Patent No. 4,003,894     Dated Jan. 18, 1977

Inventor(s) JAN VERWEIJ, HONG SHENG TAN and HERMANUS JACOBUS KOOREMAN

It is certified that error appears in the above-identified patent and that said Letters Patent are hereby corrected as shown below:

| Col. | Line | |
|---|---|---|
| 6 | 23 | Cancel "$C_4H_9BCl_2$, $(C_4H_9)_2BCl$, $(C_2H_5)_2AlCl$, $(C_4H_9)_2AlCl$, $C_6H_5PCl_2$," |
| 6 | about lines 45-48 | "$\underset{C_2H_5}{\overset{CH_3}{>}}C_6H_5OCOBr$," should be $\underset{C_2H_5}{\overset{--CH_3}{>}}CHOCOCl$ -- |
| 6 | about lines 60-64 | "$\underset{C_2H_5O}{\overset{CH_3}{>}}SiCl_2$" should be $\underset{C_2H_5O}{\overset{--CH_3}{>}}SiCl_2$ -- |
| 7 | 25 | After "$PCl_5$" insert --$POCl_3$, $POBr_3$, $PSBr_3$,-- |

UNITED STATES PATENT OFFICE
CERTIFICATE OF CORRECTION

Patent No. 4,003,894                    Dated Jan. 18, 1977

Inventor(s) JAN VERWEIJ, HONG SHENG TAN and HERMANUS JACOBUS KOOREMAN

It is certified that error appears in the above-identified patent and that said Letters Patent are hereby corrected as shown below:

| Col. | Line | |
|------|------|---|
| 8 | 50 | "isoxazolicarboxamido" should be --isoxazolecarboxamido-- |
| 16 | 56&57 | "(27 moles)" should be --(27 mmoles)-- |
| 30 | Claim 1 | Left out following formula |

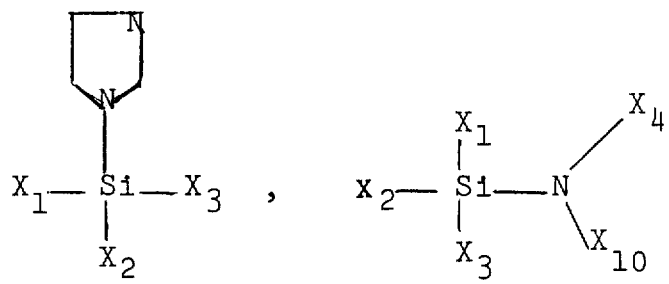

and

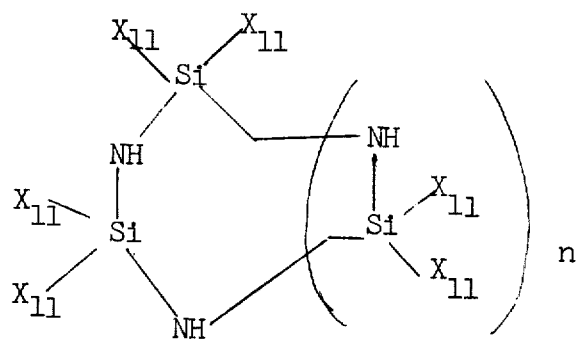

UNITED STATES PATENT OFFICE
CERTIFICATE OF CORRECTION

Patent No. 4,003,894      Dated Jan. 18, 1977

Inventor(s) JAN VERWEIJ, HONG SHENG TAN and HERMANUS JACOBUS KOOREMAN

It is certified that error appears in the above-identified patent and that said Letters Patent are hereby corrected as shown below:

| Col. | Line | | |
|---|---|---|---|
| 30 | Claim 1, 47 | "$-Si\ (X_1,$" should be $-Si\equiv(X_1--$ | |
| 30 | Claim 3 | Should read --The process of claim 1 wherein the temperature employed during ring enlargement is between 50°C and 160°C-- | |

Signed and Sealed this ninth Day of August 1977

[SEAL]

Attest:

RUTH C. MASON
*Attesting Officer*

C. MARSHALL DANN
*Commissioner of Patents and Trademarks*

UNITED STATES PATENT OFFICE
CERTIFICATE OF CORRECTION

Patent No. 4,003,894          Dated January 18, 1977

Inventor(s) JAN VERWEIJ, HONG SHENG TAN and HERMANUS JACOBUS KOOREMAN

It is certified that error appears in the above-identified patent and that said Letters Patent are hereby corrected as shown below:

SUTSTITUTE CERTIFICATE OF CORRECTION

| Col. | Line  |   |
|------|-------|---|
| 6    | 23    | Cancel "$C_4H_9BCl_2, (C_4H_9)_2BCl, (C_2H_5)_2AlCl, (C_4H_9)_2AlCl, C_6H_5PCl_2,$" |
| 6    | 45-48 | "$\begin{array}{c}CH_3\\ \diagdown\\ C_6H_5OCOBr,\\ \diagup\\ C_2H_5\end{array}$" should be -- $\begin{array}{c}CH_3\\ \diagdown\\ CHOCOCl\\ \diagup\\ C_2H_5\end{array}$ -- |
| 6    | 61-64 | "$\begin{array}{c}CH_3\\ \diagdown\\ SiCl_2\\ \diagup\\ C_2H_5O\end{array}$" should be -- $\begin{array}{c}CH_3\\ \diagdown\\ SiCl_2\\ \diagup\\ C_2H_5O\end{array}$ -- |

UNITED STATES PATENT OFFICE
CERTIFICATE OF CORRECTION

Patent No. 4,003,894     Dated Jan. 18, 1977

Inventor(s): JAN VERWEIJ, HONG SHENG TAN and HERMANUS JACOBUS KOOREMAN

It is certified that error appears in the above-identified patent and that said Letters Patent are hereby corrected as shown below:

| Col. | Line | |
|---|---|---|
| 7 | 25 | After "$PCl_5$" insert -- $POCl_3$, $POBr_3$, $PBr_3$, -- |
| 8 | 50 | "isoxazolicarboxamido" should be -- isoxazolecarboxamido -- |
| 16 | 56&57 | "(27 moles)" should be -- (27 mmoles) -- |
| 30 | Claim 1 Line 19 | Left out following formula |

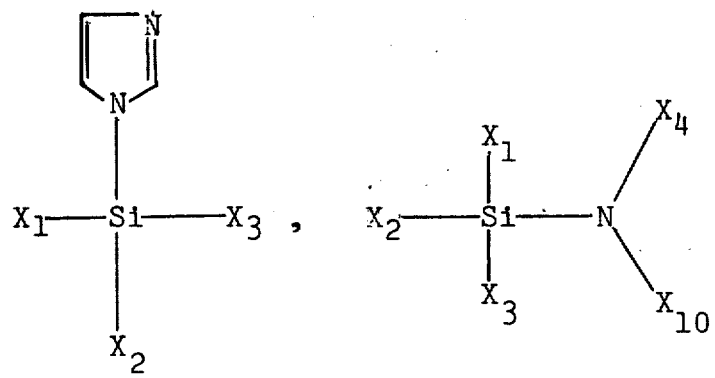

and

UNITED STATES PATENT OFFICE
CERTIFICATE OF CORRECTION

Patent No. 4,003,894  Dated Jan. 18, 1977

Inventor(s) JAN VERWEIJ, HONG SHENG TAN and HERMANUS JACOBUS KOOREMAN

It is certified that error appears in the above-identified patent and that said Letters Patent are hereby corrected as shown below:

| Col. | Line | | |
|---|---|---|---|
| 30 | Claim 1 Line 19 | 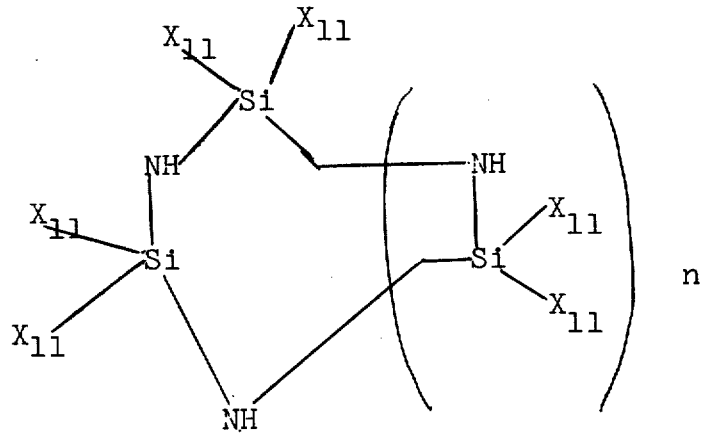 | |
| 28 | Claim 1 Line 58 | "phenyl alkyl" should be | -- phenylalkyl -- |
| 28 | Claim 1 Line 66 | "phosphorous" should be | -- phosphorus -- |
| 29 | Claim 1 Line 18 | "or $R_4$ and $R_5$ or $R_6$" should be | -- and $R_4$ with $R_5$ or $R_6$ -- |

UNITED STATES PATENT OFFICE
CERTIFICATE OF CORRECTION

Patent No. 4,003,894     Dated Jan. 18, 1977

Inventor(s) JAN VERWEIJ, HONG SHENG TAN and HERMANUS JACOBUS KOOREMAN

It is certified that error appears in the above-identified patent and that said Letters Patent are hereby corrected as shown below:

| Col. | Line |  |
|---|---|---|
| 29 | Claim 1 Line 41 | "phosphorous" should be<br><br>-- phosphorus -- |
| 29 | Claim 1 Line 61 | "... from an amine" is the end of paragraph e. "... in a dry ..." etc. continues the description of the actual process "comprising heating a 6β-acylamidopenicillanic sulfoxide acid anhydride ... in a dry inert organic solvent ...", and should be set against the left margin of column 29. |
| 30 | Claim 1 Line 8 | " 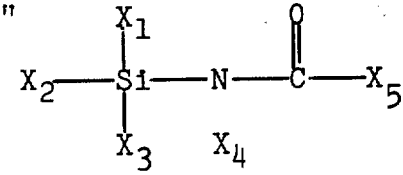 " <br><br>should be<br><br>-- 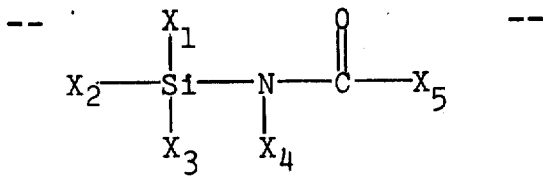 -- |

UNITED STATES PATENT OFFICE
CERTIFICATE OF CORRECTION

Page 5 of 6 pages

Patent No. 4,003,894     Dated January 18, 1977

Inventor(s) JAN VERWEIJ, HONG SHEN TAN and HERMANUS JACOBUS KOOREMAN

It is certified that error appears in the above-identified patent and that said Letters Patent are hereby corrected as shown below:

| Col. | Line | | | |
|---|---|---|---|---|
| 30 | Claim 1 Line 47 | | | " —Si ($X_1$," should be -- —Si≡($X_1$, -- |
| 30 | Claim 3 | | | Should read -- The process of claim 1 wherein the temperature employed during ring enlargement is between 50°C and 160°C. -- |
| 31 | Claim 6 Line 8 | 54 | Claim 6 Line 4 | " >$M_1$ " should be -- >$M_1$- -- |
| 31 | Claim 12 Line 51 | 55 | Claim 12 Line 5 | "$SnBr_4 PBr_5$" should be -- $SnBr_4, PBr_5$ -- |

UNITED STATES PATENT OFFICE
CERTIFICATE OF CORRECTION

Patent No. 4,003,894     Dated January 18, 1977

Inventor(s) JAN VERWEIJ, HONG SHENG TAN and HERMANUS JACOBUS KOOREMAN

It is certified that error appears in the above-identified patent and that said Letters Patent are hereby corrected as shown below:

| Col. | Line | | |
|---|---|---|---|
| 31, | Claim 13 Line 55 | 55 | "N,O,-bis" should be<br>-- N,O-bis -- |
| 32 | Claim 14 lines 2-3 | | "trimethylsilylamine" should be<br>-- triphenylsilylamine -- |

This Certificate supersedes Certificate of Correction issued August 9, 1977.

Signed and Sealed this

Ninth Day of January 1979

[SEAL]

Attest:

RUTH C. MASON
Attesting Officer

DONALD W. BANNER
Commissioner of Patents and Trademarks